United States Patent [19]

Mallet

[11] Patent Number: 5,465,323
[45] Date of Patent: Nov. 7, 1995

[54] METHOD FOR MODELLING A SURFACE AND DEVICE FOR IMPLEMENTING SAME

[75] Inventor: Jean-Laurent Mallet, Nancy, France

[73] Assignees: Association Scientifique pour la Geologie et de ses Applications, Nancy; Societe National Elf Aquitaine (Production), Courbevoie; Total Compagnie Francaise des Petroles, Puteaux; Compagnie Generale de Geophysique, Massy, all of France

[21] Appl. No.: 689,044

[22] PCT Filed: Sep. 19, 1990

[86] PCT No.: PCT/FR90/00676

§ 371 Date: May 20, 1991

§ 102(e) Date: May 20, 1991

[87] PCT Pub. No.: WO91/04544

PCT Pub. Date: Apr. 4, 1991

[30] Foreign Application Priority Data

Sep. 20, 1989 [FR] France ................................ 89 12341

[51] Int. Cl.$^6$ ................................................ G06T 17/00
[52] U.S. Cl. ........................ 395/123; 395/120; 364/421
[58] Field of Search ................................ 395/119, 120, 395/123, 141, 142; 364/413.17, 421

[56] References Cited

U.S. PATENT DOCUMENTS 4,930,092  5/1990  Reilly .................................... 395/123

FOREIGN PATENT DOCUMENTS 0196665  1/1986  European Pat. Off. .

OTHER PUBLICATIONS

"A New Method of Interpolation and Smooth Curve Fitting Based on Local Procedures" H. Akima; J. ACM 17.1 1984.
"Machine Contouring Using Minimum Curvature" I. Briggs; Geophysics 17.1, 1984.
"Triangular Bernstein–Bezier Patches", G. Farin; Computer–aided Geometric Design, Aug. 1986.
"Primitives for the Manipulation of General Subdivisions and the Computation of Voronoi Diagrams" L. Guibas et al; ACM transactions on Graphics, Apr. 1985.
"Three–dimensional Graphic Display of Disconnected Bodies"; J. Mallet; Mathematical Geology, 1988.
"Geometric Modeling and Geostatistics" J. Mallet; Geostatistics, 1989.
"Discrete Smooth Interpolation", J. Mallet' ACM Transactions on Graphics, Apr. 1989.
"Geometric Modeling", M. Mortenson; 1985.
"FEM Shape Optimization: A Case for Interactive Graphics", S. Singh, et al; Computers and Graphics, 1982.

*Primary Examiner*—Mark K. Zimmerman

[57] ABSTRACT

A method for obtaining a model of a surface including the steps of obtaining measurements of geometrical data concerning specific points on the surface, making a grid of the surface, with the grid passing through said points, memorizing, at an address which is specific to each node of the grid, the coordinates of the node, the number of satellites of the node, information for access to the addresses of said satellites and thereafter to information which relates to them, and geometrical data which may be associated with said node; for each node, defining a local roughness index obtained from a weighted sum of the current coordinates of the node and its satellites, defining the sum of an overall roughness index representing the sum of all the local roughness indices, and of an overall index of the infringement of said geometrical data, iteratively adjusting the coordinates of indefinite nodes, by using at each adjustment the sum of a weighted combination of current node neighbor coordinates and of a combination of geometrical data associated with the node, in order to minimize said sum, and creating a model of the surface on the basis of the adjusted coordinates.

16 Claims, 8 Drawing Sheets

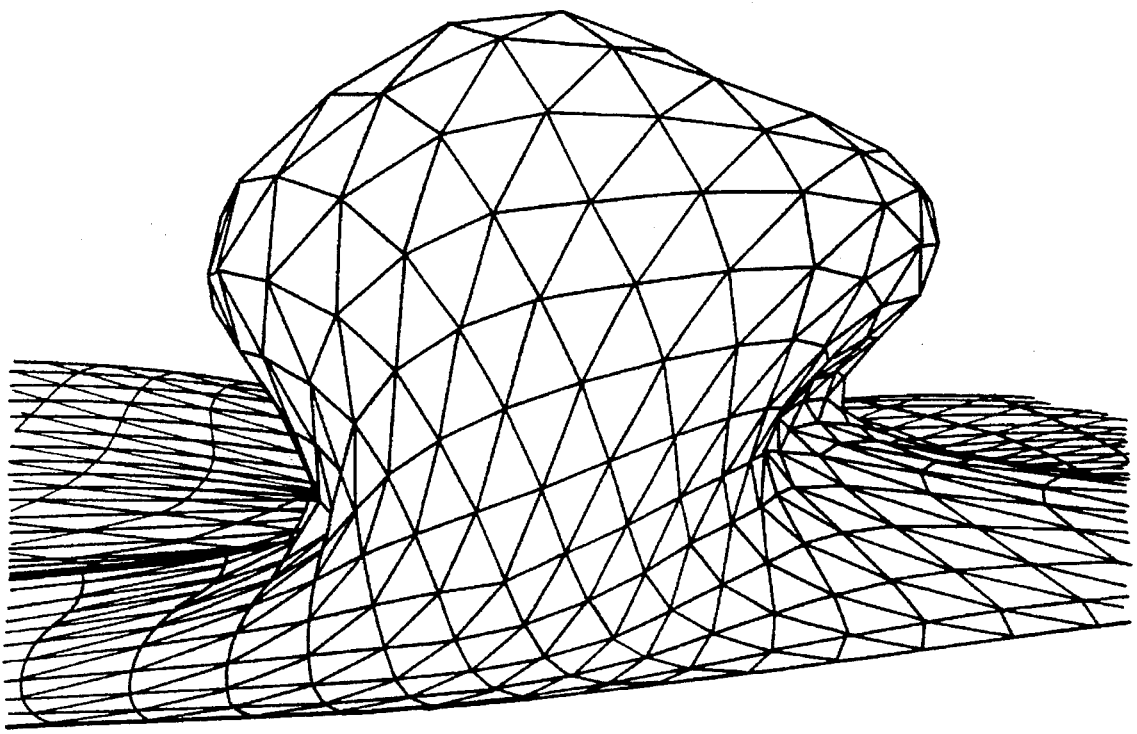
FIG_3

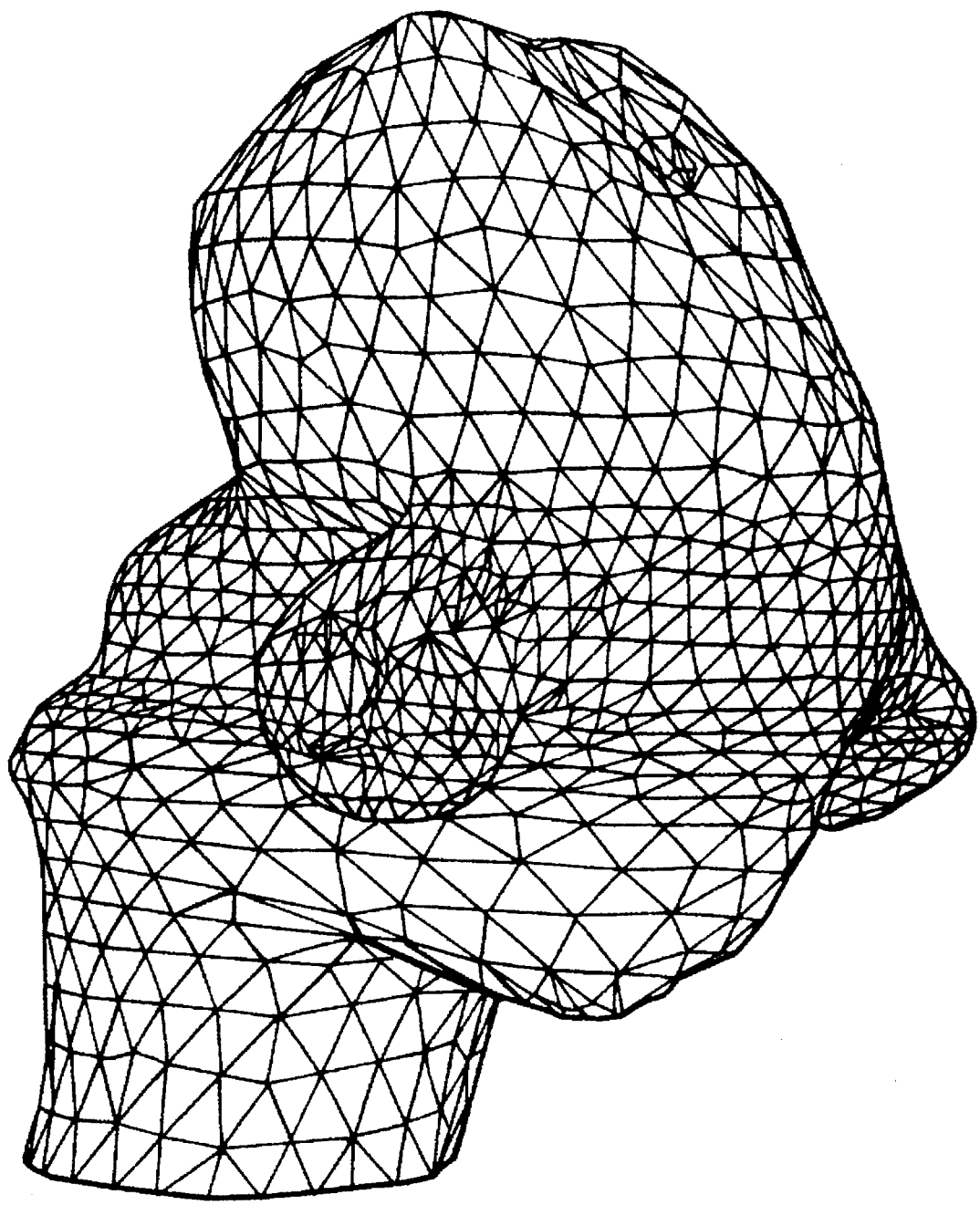
FIG_4

METHOD FOR MODELLING A SURFACE AND DEVICE FOR IMPLEMENTING SAME

SUMMARY OF THE INVENTION

The present invention is generally concerned with investigations within a three-dimensional body and is particularly concerned with a new process of obtaining a representation of a surface within a body on the basis of a limited set of known geometrical data relating to said surface.

Investigations within three-dimensional bodies are of major concern in geology, geophysics and biology.

In geophysics, for example, it is necessary to obtain as accurate as possible representations of surfaces situated, for example, at the interface between two areas of different kinds or with different properties, on the basis of data obtained from prospecting, or during exploitation of an underground resource.

How effectively the three-dimensional body is investigated, especially in prospecting for oil or other underground resources, depends on the accuracy with which this type of surface can be reconstituted and represented.

In medicine and biology there are various known processes for obtaining representations of cross-sections through a living body or the like and the aim is also to reconstitute and represent in three dimensions a surface situated at the interface between two media, for example the contours of a bodily organ.

There already exist a number of modeling techniques for obtaining a representation of a surface within a three-dimensional body that is to be exploited or treated. Particularly worthy of mention are the Bézier interpolation method and the spline functions method (for more details reference should be had to Geometric Modeling, M. E. Mortenson, Ed. John Wiley, 1985).

However, all these known techniques are ill suited to handling heterogeneous data, by which is meant data relating to the coordinates of points on the surface, to fixed orientations of the surface, to geometrical links between two separate points, etc. Also, these techniques are ill-suited to a wide spread of surfaces or to surface anomalies such as folds and breaks, and to discontinuous surfaces. To be more precise, in some cases the functions used in these techniques are not convergent or have no solution or have no single solution.

Finally, the known techniques are not able to take into account the concept of the degree of certainty with which some surface data is known.

The present invention is directed to alleviating the drawbacks of the prior art processes and to proposing a process that can allow for non-homogeneous and/or highly diverse geometrical data and for the anomalies mentioned above and other anomalies, providing in each case a single and unambiguous model of the surface.

Another object of the invention is to propose a process that can use geometrical data and at the same time data as to the degree of certainty or accuracy of said data.

To this end, the present invention firstly consists in a process for modeling a surface representing for example the interface between two areas of different kinds or with different properties in a three-dimensional body such as a geological formation or a living body, characterized in that it comprises the steps of:

obtaining by means of measuring apparatus a set of geometrical data relating to the surface and associated with respective points on said surface;

meshing the surface so that all said points are a subset of the nodes of the mesh;

storing at a specific memory address for each node of the mesh, the following data:

the coordinates of the node in question, the number of satellite nodes of the node in question, data providing access to the specific addresses of said satellite nodes and consequently to the data relating thereto, if necessary, geometrical data associated with said node in question, for each node of the mesh, defining a local roughness index derived from a weighted sum of the actual coordinates of the node and of its satellites, defining the sum of a global roughness index obtained by summing the local roughness indices associated with each node and a global index of violation of said geometrical data, fitting the coordinates of each node for which the precise coordinates are not known by an iterative method in which for each step of the iteration there are added a weighted combination of the actual coordinates of the satellite and of the satellites of the satellites of said node and a combination of the geometrical data associated with said node, in such a way as to minimize said sum, and creating a representation of the surface from the fitted coordinates of each node.

The invention also concerns a device for modeling a surface representing for example the interface between two areas of different kinds or with different properties in a three-dimensional body such as a geological formation or a living body, characterized in that it comprises:

means for obtaining by means of measuring apparatus a set of geometrical data relating to the surface and associated with respective points on said surface;

means for meshing the surface so that all said points are a subset of the nodes of the mesh;

means for storing at a specific memory address for each node of the mesh, the following data:

the coordinates of the node in question, the number of satellite nodes of the node in question, data providing access to the specific addresses of said satellite nodes and consequently to the data relating thereto, if necessary, geometrical data associated with said node in question, calculation means for fitting the coordinates of each node for which the precise coordinates are not known by an iterative method in which for each step of the iteration there are added a weighted combination of the actual coordinates of the satellite and of the satellites of the satellites of said node and a combination of the geometrical data associated with said node, in such a way as to minimize a sum of a global roughness index obtained by summing local roughness indices associated with each node and each derived from a weighted sum of the actual coordinates of the node and of its satellites and a global index of violation of said geometrical data, means for creating a representation of the surface from the fitted coordinates of each node.

These and other objects of the present invention will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will emerge more clearly from the following detailed description of one preferred embodiment of the invention given by way of non-limiting example and with reference to the appended drawings, in which:

FIG. 3 shows a typical complex geological surface (salt dome) modeled using the process of the present invention;

FIG. 4 shows a typical complex biological surface (embryo brain) modeled using the process of the present invention from discrete data obtained from a succession of cross-sections;

Identical or similar elements or parts are designated by the same reference numbers in all the figures.

DETAILED DESCRIPTION OF PREFERRED EMBODIMENT

Figure 1:
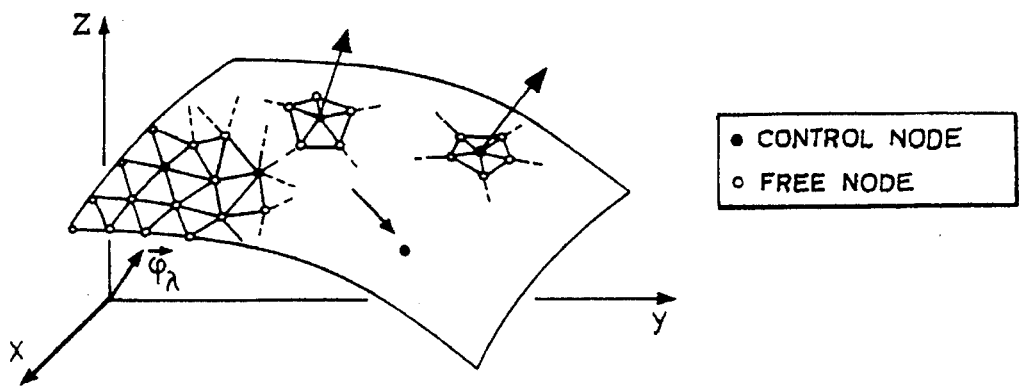
FIG. 1 shows a typical graph incorporating meshing used to model a surface, this graph being defined by the set of all the sides of facets whose vertices constitute the set $\Omega$ described later, and also shows arrows symbolically representing displacements of nodes of the mesh applied interactively by the user to shape the surface.

Reference will be made later to a number of publications whose respective contents are deemed to be included by way of reference into this description.

(1) A method of Bivariate interpolation and smooth surface fitting based on local procedures, H. AKIMA, J. ACM 17.1, 1974;

(2) Shape reconstruction from planar cross-sections, J. D. BOISSONNAT, ACM Transactions on Graphics, vol. No. 2, 1986;

(3) Machine contouring using minimum curvature, I. C. BRIGGS, Geophysics 17.1, 1974;

(4) Triangular Bernstein-Bézier patches, G. FARIN, Computer-aided geometric design, 1986;

(5) Primitives for the manipulation of general subdivisions and the computation of Voronoi diagrams, L. GUIBAS and J. STOLFI, ACM transactions on Graphis, vol. No. 2, 1985;

(6) Three-dimensional graphic display of disconnected bodies, J. L. MALLET, Mathematical Geology, vol. 20, no. 8, 1988;

(7) Geometrical modeling and geostatistics, J. L. MALLET, Proceedings of the Third International Geostatistics Congress, Kluwer Academic Publishers, 1989;

(8) Discrete Smooth Interpolation, J. L. MALLET, ACM Transactions on Graphics, April issue, 1989;

(9) Geometric Modeling, M. E. MORTENSON, John Wiley, 1985.

Also, the following description of one preferred embodiment of the invention is followed by section 2, infra explaining a method of reconstituting a surface derived from the method explained in reference document (8) and on which the process of the present invention is based.

1. DESCRIPTION OF A PROCESS IN ACCORDANCE WITH THE INVENTION FOR ENCODING AND FITTING COMPLEX SURFACES

1.1 Introduction

1.1.1 Nature of the process

An industrial process described hereafter is used to encode and fit complex surfaces encountered, for example, when modeling:

- interfaces between different domains,
- interfaces between geological layers,
- interfaces between biological organs,
- etc.

The result of this encoding phase may be converted into pictures and/or solid models (molded from plastics material, for example) by a graphic computer or any other device. In geology, for instance, these pictures and/or solid models are used to optimize the prospecting, exploitation and management of earth resources such as:

- oil deposits,
- mineral deposits,
- water deposits,
- etc.

The process described hereafter consists of two complementary sub-processes:

1. a sub-process to encode a surface,
2. a sub-process to fit a surface to the data currently available. In geology, for example, these data may be:
   - the exact or approximate location of points in the intersection of a given surface and a plane,
   - the exact or approximate location of the intersection of a well and a geological surface corresponding to the interface between two geological layers,
   - the exact or approximate location of the plane tangent to a geological surface corresponding to the interface between two geological layers,
   - the exact or approximate throw vector of a fault breaking the geological surface corresponding to the interface between two geological layers,
   - etc.

The encoding process is designed to optimize the fitting process based on a new version of the DSI method (cf. [8]) especially developed for the geometrical modeling of surfaces. This new version of the DSI method, which has not yet been published, is presented in section 2, infra.

1.1.2 Dividing a surface into facets

Let S be the surface to model. As shown in FIG. 1 and as explained in [6] and [7], this surface will be approximated by a set of triangular and/or polygonal facets. These facets are characterized by:

The coordinates of their vertices. These vertices constitute a finite set of N points $\{\vec{\phi}_1, \ldots, \vec{\phi}_N\}$ regularly distributed on S and numbered from 1 to N. The coordinates of the $k^{th}$ vertex $\vec{\phi}_k$ will be denoted $(\phi_k^x, \phi_k^y, \phi_k^z)$.

Their edges constituting the links between pairs of vertices $(\vec{\phi}_i, \vec{\phi}_j)$.

The set of edges of the triangles and/or polygons composing the surface S constitute a graph G whose nodes are the vertices of the triangles and/or polygons. For this reason and for the sake of simplicity, "node" is used hereafter as a synonym of "vertex of triangles and/or polygons".

$$\text{node} \uparrow \{\text{vertex of triangles and/or polygons}\}$$

1.1.3 Preliminary definitions

Set of satellites $\Lambda(k)$

Let $\vec{\phi}_k$ be the $k^{th}$ node of a surface S. The "set of satellites" of $\vec{\phi}_k$ is the set $\Lambda(k)$ Of the nodes $\vec{\phi}_j$ different from $\vec{\phi}_k$ and such that $(\vec{\phi}_j, \vec{\phi}_k)$ iS an edge of triangle or polygon. In other words, the set $\Lambda(k)$ is such that:

$$\begin{vmatrix} 1) \Lambda(k) = \{\phi_{j1}, \ldots, \phi_{jn_k}\} \\ 2) \phi_j \in \Lambda(k) \Longleftrightarrow \begin{cases} \phi_j \text{ and } \phi_k \text{ define an edge of a triangle} \\ \text{or polygon} \end{cases} \end{vmatrix}$$

As shown above, the number of satellites attached to the node $\vec{\phi}_k$ is denoted $n_k$.

The orbit concept discussed in the articles [6] and [7] has not yet been subjected to any particular encoding process; an important feature of the invention is its proposed method of encoding $\Lambda(k)$.

Neighborhood N(k)

Let $\vec{\phi}_k$ be the $k^{th}$ node of a surface S. The neighborhood N(k) of $\vec{\phi}_k$ is the subset N(k) of nodes equal to the union of $\vec{\phi}_k$ and its satellites. In other words:

$$N(k) = \{\vec{\phi}_k\} \cup \Lambda(k)$$

A neighbor of node $\vec{\phi}_k$ is any node belonging to the set N(k). Thus:

$$\vec{\phi}_j \in N(k) \Longleftrightarrow \{\vec{\phi}_j = \text{Neighbor of } \vec{\phi}_k\}$$

The neighborhood concept discussed in the articles [7] and [8] has not yet been subjected to any particular encoding process; an important feature of the invention is its proposed method of encoding N(k).

Atom A(R) and associated kernel

Let $\vec{\phi}_k$ be the $k^{th}$ node of a surface S. The atom of kernel $\vec{\phi}_k$ A(R) is the pair $(\vec{\phi}_k, \Lambda^*(k))$ composed of:

the node $\vec{\phi}_k$ the set $\Lambda^*(K)$ of the addresses or the codes $\{A^*(j1), \ldots, A^*(jn_k)\}$ allowing the set of the corresponding atoms $\{A(j1), \ldots, A(jn_k)\}$ whose kernels are the satellites of $\vec{\phi}_k$ to be retrieved from a memory.

In other words:

$$\begin{vmatrix} A(k) = (\vec{\phi}_k, \Lambda^*(k)) = (\vec{\phi}_k, \{A^*(j_1), \ldots, A^*(j_{n_k})\}) \\ \text{with:} \begin{cases} n_k = \text{number of satellites of } \vec{\phi}_k \\ A^*(j) = \text{Address or access code of the atom } A(j) \\ \phantom{A^*(j) =} \text{corresponding to the kernel of the } j^{th} \\ \phantom{A^*(j) =} \text{satellite of } \vec{\phi}_k \end{cases} \end{vmatrix}$$

The atom concept discussed in the article [6] has not yet been subjected to any particular encoding process; an important feature of the invention is its proposed method of encoding A(k).

Constraints and types of constraints

A constraint attached to an atom A(k) is any condition concerning the location of the node $\vec{\phi}_k$ corresponding to the kernel of this atom. For example, in geology, the following constraints are of prime importance to fitting a surface to precise or imprecise data observed or measured by a manual or geophysical technique:

The coordinates $(\phi_k^x, \phi_k^y, \phi_k^z)$ of the node $\vec{\phi}_k$ are known exactly. Such a constraint is called a control node type constraint and may be used in geology to encode the intersection of the modeled surface with a well.

The coordinates $(\phi_k^x, \phi_k^y, \phi_k^z)$ of the node $\vec{\phi}_k$ are not known exactly but with a given certainty factor. Such a constraint is called a fuzzy control node type constraint and may be used to encode the approximate location of a node of the modeled surface measured approximately by a given process. For example, seismic data in geology, and data corresponding to sections of organs observed with a microscope or using ultrasound techniques or with a scanner in biology are of this type.

The vector $(\vec{\phi}_\lambda - \vec{\phi}_k)$ joining the node $\vec{\phi}_k$ to another node $\vec{\phi}_\lambda$ is approximately known with a given certainty factor. Such a constraint is called a fuzzy vectorial link type constraint and is used in geology, for example, to encode the throw vector of a fault, the nodes $\vec{\phi}_k$ and $\vec{\phi}_\lambda$ being on opposite sides of the fault (see FIG. 2).

The vector $\vec{V}$ orthogonal to the tangent plane to the surface S at node $\vec{\phi}_k$ is approximately known with a given certainty factor. Such a constraint is called a fuzzy vector normal type constraint and is used in geology, for example, to encode the plane tangent to layer interfaces measured by a manual or geophysical technique (sounding).

Etc.

The certainty factors mentioned above are positive numbers whose values are assumed to be proportional to the a priori confidence that can be attached to the corresponding data. Accounting for these fuzzy constraints constitutes one of the characteristics of the invention and is described in detail in section 2 (see sections 2.5 and 2.7.6), infra.

Notation

To simplify, no distinction will be drawn between the number of any node of a surface and the node itself. This implies that:

$\Lambda(k)$=set of satellites $\{\vec{\phi}_{j1}, \ldots, \vec{\phi}_{jn_k}\}$ of $\vec{\phi}_k$ or set of corresponding numbers $\{j1, \ldots, jn_k\}$, N(k)=set of neighbors $\{\vec{\phi}_k, \vec{\phi}_{j1}, \ldots, \vec{\phi}_{jn_k}\}$ of $\vec{\phi}_k$ or set of corresponding numbers $\{k, j1, \ldots, jn_k\}$.

1.1.4 State of the art

Classical methods

A complete description of the "state of the art" concerning the modeling of complex surfaces is given in reference [7]. This article explains precisely why the classical methods used in automatic mapping and in Computer Aided Design (CAD) are not relevant to the modeling of complex surfaces, as might otherwise be expected. The basics of the DSI method (also known as the DSI/DSA method) which overcomes these difficulties are briefly introduced at the end of reference [7].

The DSI method

This method is based on the notion of "roughness" of a surface S composed of triangular and/or polygonal facets. This notion of "roughness" $R(\phi|k)$ at node $\vec{\phi}_k$ of a surface S is defined as follows (See ref. [7], [8] and appendix):

$$R(\phi|k) = \sum_{\alpha \in N(k)} v^\alpha(k) \cdot \phi_\alpha^2$$

The positive or null coefficients $\{v^\alpha(k)\}$ occurring in this definition are weighting coefficients chosen by the user. Among the infinity of possible choices, one of the most interesting, called "harmonic weighting", consists of choosing:

$$v^\alpha(k) = \begin{cases} -|\Lambda(k)| & \text{if } \alpha = k \\ 1 & \text{if } \alpha \in \Lambda(k) \end{cases}$$

The local roughnesses so defined are then combined in a global roughness $R(\vec{\phi})$:

$$R(\vec{\phi}) = \sum_k \mu(k) \cdot R(\phi|k)$$

The positive or null coefficients $\mu(k)$ occurring in this definition are used to modulate the contribution of the local roughness $(R(\vec{\phi}|k)$ to the global roughness $R(\vec{\phi})$. If a uniform weighting is used, for example:

$$\mu(k) = 1 \forall k$$

Among other possible choices for the coefficients $\mu(k)$, the following weightings can be used, where m is a given positive constant:

$$\mu(k) = \begin{cases} 1 \text{ if } \phi_k \text{ is a data point,} \\ m > 1 \text{ if } \phi_k \text{ is not a data point.} \end{cases}$$

The principle of the DSI method consists in computing the location of each node $\vec{\phi}_k$ of the surface S to model in order to render it as smooth as possible while respecting the data and constraints governing the shape of the surface. The paper [8] is devoted to a mathematical presentation of the DSI method and proposes a technique for minimizing the global roughness while respecting the data and constraints.

Interactive version Of the DSI method

The method proposed in [8] for minimizing the global roughness is not well suited to interactive use on an electronic computer (or microprocessor), which is why section 2, infra proposes a new method on which the invention is based. As mentioned previously, the object of the invention is to propose an encoding and fitting process for the surface S based on this new version of the DSI method.

1.2 Examples of images of objects encoded and fitted with the process

1.2.1 Geological example

Oil prospecting is generally performed indirectly in the sense that one is looking for geological layers which could have acted as a trap for oil; for example, deformations of salt layers called "salt domes" are generally excellent oil traps. In order to locate the oil precisely, it is necessary to know the exact shape of the "trap" layers and unfortunately, in many cases, until now there was no practical process usable to model it efficiently. The salt dome case is generally regarded as the most complex and that is why to prove the efficiency of this encoding and fitting process FIG. 3 shows an image of such a surface obtained with it.

1.2.2 Biological example

Medical data acquisition processes (scanner or ultrasound) are mathematically identical to seismic techniques used in oil prospecting. For example, the ultrasound technique is identical to seismic reflection and scanners are based on tomography as in seismic tomography. This is one reason why this encoding and fitting process may be used to model the skin of biological organs. FIG. 4 shows a model of the brain of a 7 millimeters long human embryo obtained using this encoding and fitting method. Note that until now organs this small (the brain is 1 millimeter long) could only be seen in the form of microscopic sections.

1.3 Encoding process for a surface S

1.3.1 Memory and memory address concepts

The term "memory" denotes any electronic computing device able to record data, codes or partial results and to retrieve them on request for use in subsequent operations. Moreover, the "address" of a memory is any code identifying the physical location of the memory inside the computer.

1.3.2 Encoding an atom A(k)

The following process or one of its variants may be used to encode and store each atom A(k) in a set of memories:

Encoding process

Figure 5:
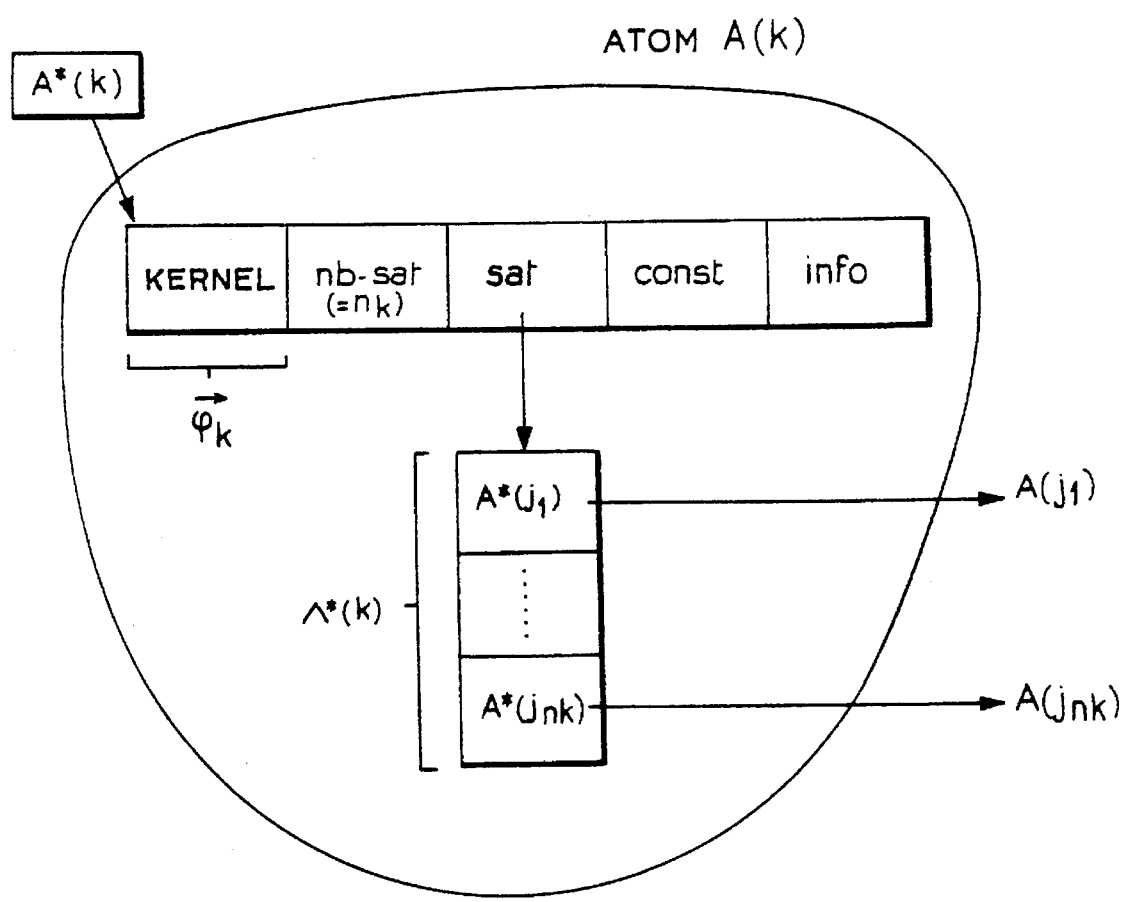
FIG. 5 shows the organization of the memory associated with an atom A(k) of the kernel $\vec{\phi}_k$.

As suggested in FIG. 5, a contiguous memory area beginning at address A*(k) stores consecutively the following data relating to the atom A(k) corresponding to the node $\vec{\phi}_k$:

1. Kernel=
    either the coordinates $(\phi_k^x, \phi_k^y, \phi_k^z)$ of the node $\vec{\phi}_k$,
    or the address or the code or any other data allowing the coordinates $(\phi_k^x, \phi_k^y, \phi_k^z)$ of the node $\vec{\phi}_k$ to be retrieved.
2. nb_sat=
    either the number $n_k$ of satellites linked to the node $\vec{\phi}_k$,
    or the address or the code or any other data allowing the number $n_k$ of satellites linked to the node $\vec{\phi}_k$ to be retrieved.
3. Sat=
    Address of a memory area containing the addresses or the access codes $\{A^*(j1), \ldots, A^*(jn_k)\}$ allowing the $n_k$ atoms $\{A(j1), \ldots, A(jn_k)\}$ whose kernels $\{\vec{\phi}_{j1}, \ldots, \vec{\phi}_{jn_k}\}$ are the satellites of the node $\vec{\phi}_k$ to be retrieved.
4. Const=
    Encoded constraints (see section 1.1.3) attached to the node $\vec{\phi}_k$. This encoding will be explained in detail in section 1.1.3.
5. Info=
    Memory area of variable size that can contain complementary data concerning the atom A(k). This data is specific to each particular application; for instance, in oil prospecting, if A(k) is an atom of the surface separating two adjacent layers C1 and C2, then it may be interesting to store in the Info field:

- a list of physical properties (porosities, seismic velocities, etc) of the layer C1 at node $\vec{\phi}_k$ corresponding to the atom A(k),
- a list of physical properties (porosities, seismic velocities, etc) of the layer C2 at node $\vec{\phi}_k$ corresponding to the atom A(k),
- a list of geological properties (geological facies, presence of oil, etc) of the layer C1 at node $\vec{\phi}_k$ corresponding to the atom A(k),
- a list of geological properties (geological facies, presence of oil, etc) of the layer C2 at node $\vec{\phi}_k$ corresponding to the atom A(k),
- etc.

Variant 1

Figure 6:
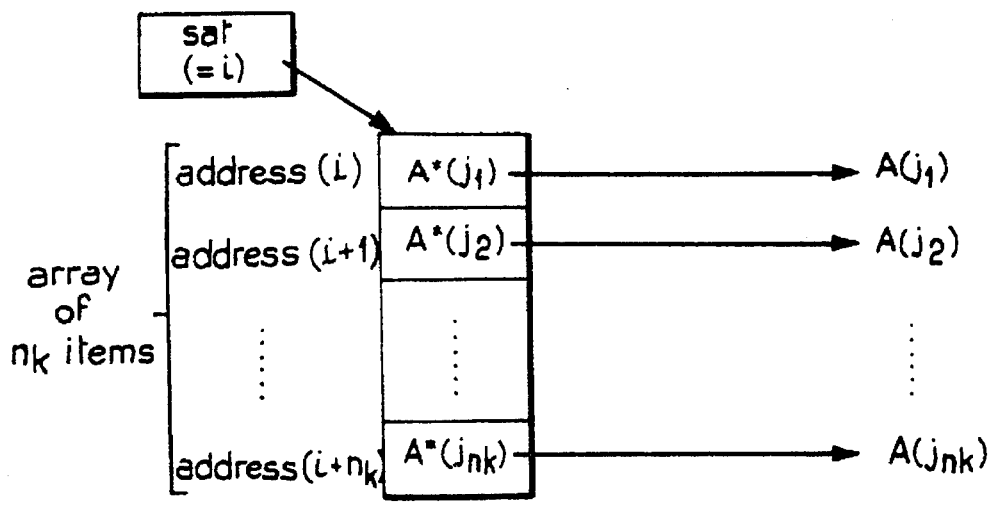
FIG. 6 shows a first example of memorizing an orbit of a given atom in an array with $n_k$ items.
Figure 7:
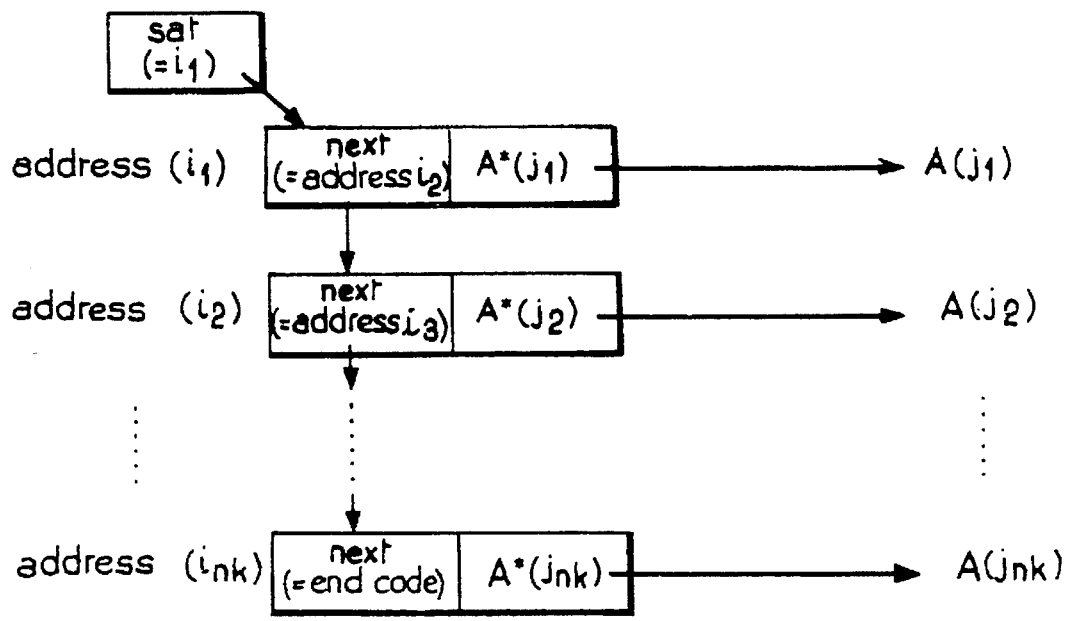
FIG. 7 shows a second example of memorizing an orbit of a given atom in $n_k$ arrays each of two items.

The memory area in which are stored the addresses or the access codes $\{A^*(j1), \ldots, A^*(jn_k)\}$ for retrieving the $n_k$ atoms $\{A(j1), \ldots, A(jn_k)\}$ whose kernels are the satellites $\{\vec{\phi}_{j1}, \ldots, \vec{\phi}_{jn_k}\}$ of the node $\vec{\phi}_k$ may be structured in two ways:

1. As shown in FIG. 6, the first way consists in using an array composed of $n_k$ consecutive memories containing the addresses $\{A^*(j1), \ldots, A^*(jn_k)\}$.
2. The second way (FIG. 7) consists in using $n_k$ arrays each containing two consecutive memories such that for the $\alpha^{th}$ array:
   - the first memory contains the address $A^*(j_\alpha)$ of the atom corresponding to the $\alpha^{th}$ satellite of the atom A(k),
   - the second memory contains the address of the $(\alpha+1)^{th}$ array. If $\alpha$ is equal to the number $n_k$ of satellites (nb_sat=$n_k$), then this second memory is either unused or contains a code specifying that the last satellite of A(k) has been reached.

Variant 2

It is possible not to store the nb_sat field but in this case, if the list of addresses or access codes $\{A^*(j1), \ldots, A^*(jn_k)\}$ iS coded as a single array (see variant 1), it is necessary to add a memory area $A^*(n_k+1)$ to store a code indicating that the list $\Lambda^*(k)$ is finished.

Variant 3

The Sat field has to be made big enough to contain the addresses or access codes $\{A^*(j1), \ldots, A^*(jn_k)\}$.

Variant 4

Many variants are possible depending on the size of the Info field and on how it is partitioned. However, it is obvious that all these variants have no influence on the use of the atom A(k) in connection with the fitting algorithm based on the DSI method described in section 2, infra.

Variant 5

Other fields can be added to the atom A(k) described above. However these other fields have no influence on the use of the atom A(k) in connection with the fitting algorithm based on the DSI method described in section, infra.

Variant 6

For any variant, what is really important for an efficient implementation of the DSI method is that the address or the access code $A^*(k)$ of a given atom A(k) should be the most direct path to the atoms whose kernels are the satellites of the kernel of A(k).

The main object of the method of encoding A(k) in a memory described above is to allow direct access to the satellites.

1.3.3 Encoding the Constraints

Each constraint relative to an atom A(k) will be stored in a specific memory area whose description follows:

Process for encoding a constraint

Figure 8:
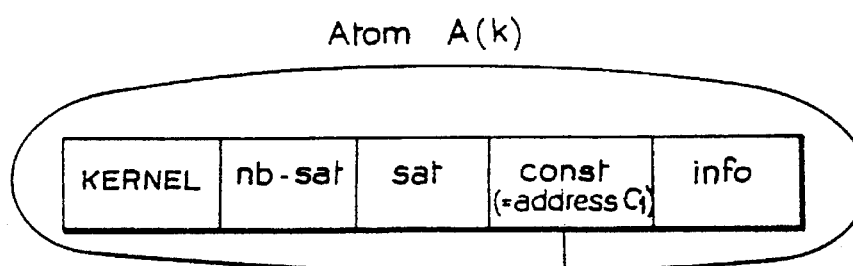
FIG. 8 shows the memorization of a geometrical datum or constraint.

As shown in FIG. 8, the encoding of a particular constraint attached to a given atom is performed in a memory area made up of two fields, Constraint and Next. These two fields are used as follows:

Constraint=
Memory area containing:
  either the data related to the encoded constraint (see below),
  or the address or the access code of a memory area containing the data related to the encoded constraint.

The data related to the encoded constraint must include a code identifying the type of the encoded constraint (see section 1.1.3).

Next=
Memory area containing:
  either a code indicating that the current constraint is the last constraint attached to the atom A(k),
  or the address of a memory area containing the next constraint (see below).

Process for storing all constraints attached to an atom

As described in section 1.3.2, encoding an atom A(k) requires a Const field that will be used to store:

either a code specifying that the atom A(k) has no constraint,
or the address of a memory area containing the first constraint related to the atom A(k).

Figure 9:
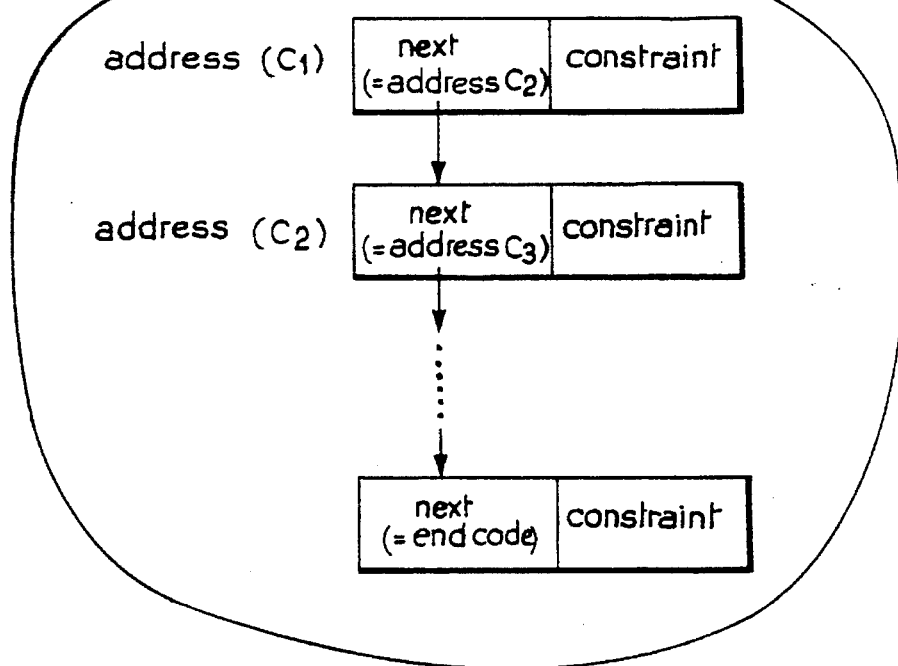
FIG. 9 shows the method of memorizing a set of geometrical data or constraints relating to a given atom A(k)

If the address of the $n^{th}$ constraint related to the atom A(k) is stored in the Next field of the $(n-1)^{th}$ constraint (n>1), then, as shown in FIG. 9, this implies that all the constraints related to A(k) are attached to A(k). This encoding process allows new constraints to be added or old constraints to be removed without modifying the organization of the other data.

Examples of data relating to a given constraint

Section 1.1.3 gives three examples of constraint types which are of prime importance for the encoding and fitting of complex surfaces encountered in biology and geology. For each of these types of constraints data has to be attached to the Constraint field previously described and shown in FIG. 9:

For a fuzzy control node type constraint, in addition to the constraint type, it is necessary to store at least the following data:
  the approximate coordinates $(\phi_k^x, \phi_k^y, \phi_k^z)$ of the node $\vec{\phi}_k$ corresponding to the kernel of the atom A(k) to which the constraint is attached,
  the certainty factor (positive number) proportional to the confidence that can be placed in the approximate coordinates $(\phi_k^x, \phi_k^y, \phi_k^z)$.

For a fuzzy vectorial link type constraint, in addition to the type, it is necessary to store at least the following data:
  the address of the node $\vec{\phi}_\lambda$ linked to the kernel $\vec{\phi}_k$ of the atom A(k) to which the constraint is attached,
  the three approximate coordinates of the vector $(\vec{\phi}_\lambda - \vec{\phi}_k)$ joining the node $\vec{\phi}_k$ to the node $\vec{\phi}_\lambda$,
  the certainty factor (positive number) proportional to the confidence that can be placed in the approximate coordinates of the vector $(\vec{\phi}_\lambda - \vec{\phi}_k)$.

For a fuzzy vector normal type constraint, in addition to the type, it is necessary to store at least the following data:
  the three approximate components of the vector $\vec{V}$ orthogonal to the surface S at the node $\vec{\phi}_k$ corresponding to the kernel of the atom A(k) to which the constraint is attached, the certainty factor (positive number) proportional to the confidence that can be placed in the approximate coordinates of the vector $\vec{V}$.

The three constraint types are described in detail in sections 2.5 and 2.7.6, infra.

Variant

Until now only one certainty factor common to the x, y and z components of each constraint has been introduced but up to three different certainty factors can be assigned to these three components.

1.3.4 Encoding a surface S

Figure 10:
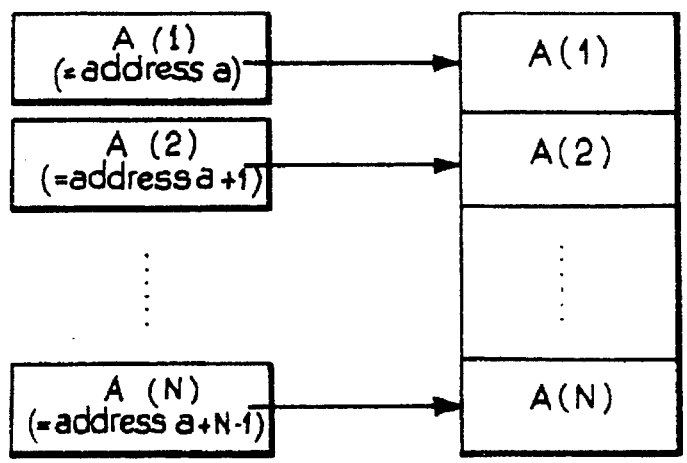
FIG. 10 shows the memorization in an array of all of the atoms relating to a surface S.
Figure 11:
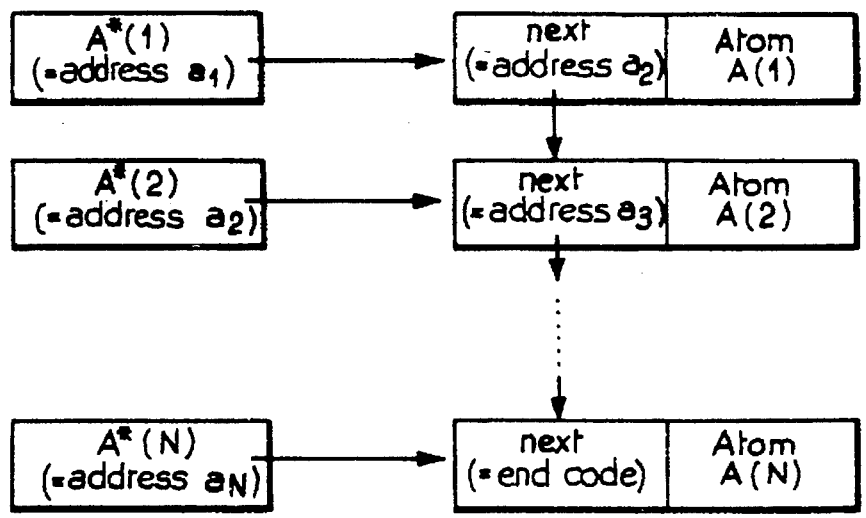
FIG. 11 shows the chaining of access to said set of atoms.

In order to optimize the programming of the variant of the DSI method presented in section 2, infra, a surface composed of triangular and/or polygonal facets is encoded as a set of N atoms whose kernels (nodes) are the vertices of the triangles and/or polygons. The data and codes for each of these atoms $\{A(1), \ldots, A(N)\}$ may be stored:

either in an array (see FIG. 10), or in the Atom field of memory areas linked by their Next field (see FIG. 11). In this case, the Next field associated with the atom number k must contain the address or the access code of the next atom numbered (k+1); the Next field associated to the last atom A(N) must contain a code indicating that the last atom has been reached.

The second solution is better if it must be possible to add and/or remove atoms easily but requires more memory than the first solution.

1.3.5 Variants

To simplify the description, the memory areas used to encode the data have been split up into fields and each of these fields has been given:

a name, a memory location.

One of ordinary skill in the art would understand that the encoding process described in this patent does not depend on the names or the order of these fields inside the memory areas used. Also, it is always possible to add new fields for particular applications without modifying the storage process.

1.4 Fitting a surface S

1.4.1 Introduction

Let S be a surface encoded according to the process described in section 1.3. There will be described hereafter a process based on this encoding to fit optimally the coordinates of some nodes $\{\vec{\phi}_1, \ldots, \vec{\phi}_N\}$ in order to:

make S as smooth as possible in relation to the global roughness criterion of the DSI method (see references [7], [8], the appendix and section 1.1.4), make S respect as much as possible the data and constraints, however accurately they may be known, concerning the shape of this surface (see sections 1.1.1 and 1.1.3).

For that purpose, we use a new variant of the DSI method described in the appendix and designed to use the encoding process described in section 1.3. Taking into account the measured or observed data, this method fits the three coordinates $(\phi_\alpha^x, \phi_\alpha^y, \phi_\alpha^z)$ of each free node $\vec{\phi}_\alpha$ successively and using an iterative method and the following formula:

new value of $\phi_\alpha^x = f_\alpha^x$(old values of $\phi_1^x, \ldots, \phi_N^x$), new value of $\phi_\alpha^y = f_\alpha^y$(old values of $\phi_1^y, \ldots, \phi_N^y$), new value of $\phi_\alpha^z = f_\alpha^z$(old values of $\phi_1^z, \ldots, \phi_N^z$).

Referring to the appendix describing the new version of the DSI method, these updating functions $f_\alpha^x(\ )$, $f_\alpha^y(\ )$ and $f_\alpha^z(\ )$ are derived from the local form of the DSI equations at point α and have the following form (see sections 2.4.1, 2.4.2 and 2.7.3, infra):

$$f_\alpha^x(\ldots) = \frac{1}{M_\alpha^x} \cdot \left\{ \sum_{k \in N(\alpha)} \left\{ \mu(k) v^\alpha(k) \cdot \sum_{\substack{\beta \in N(k) \\ \beta \neq \alpha}} v^\beta(k) \cdot \phi_\beta^x \right\} + \sum_i \{\Gamma_i^{x\alpha} - Q_i^{x\alpha}\} \right\}$$

$$f_\alpha^y(\ldots) = \frac{1}{M_\alpha^y} \cdot \left\{ \sum_{k \in N(\alpha)} \left\{ \mu(k) v^\alpha(k) \cdot \sum_{\substack{\beta \in N(k) \\ \beta \neq \alpha}} v^\beta(k) \cdot \phi_\beta^y \right\} + \sum_i \{\Gamma_i^{y\alpha} - Q_i^{y\alpha}\} \right\}$$

$$f_\alpha^z(\ldots) = \frac{1}{M_\alpha^y} \cdot \left\{ \sum_{k \in N(\alpha)} \left\{ \mu(k) v^\alpha(k) \cdot \sum_{\substack{\beta \in N(k) \\ \beta \neq \alpha}} v^\beta(k) \cdot \phi_\beta^z \right\} + \sum_i \{\Gamma_i^{z\alpha} - Q_i^{z\alpha}\} \right\}$$

$$\text{with:} \begin{cases} M_\alpha^{*x} = M_\alpha + \sum_i \gamma_i^{x\alpha} \\ M_\alpha^{*y} = M_\alpha + \sum_i \gamma_i^{y\alpha} \\ M_\alpha^{*z} = M_\alpha + \sum_i \gamma_i^{z\alpha} \\ M_\alpha = \sum_{k \in N(\alpha)} \mu(k)(v^\alpha(k))^2 \end{cases}$$

The nature and the role of the weighting coefficients $\{v^\alpha(k)\}$ and $\mu(k)$ have been discussed in section 1.1.4 and are explained in article [8] and in section 2, infra. The values of the terms $\{\Gamma_i^{x\alpha}, \Gamma_i^{y\alpha}, \Gamma_i^{z\alpha}\}$, $\{\gamma_i^{x\alpha}, \gamma_i^{y\alpha}, \gamma_i^{z\alpha}\}$ and $\{Q_i^{x\alpha}, Q_i^{y\alpha}, Q_i^{z\alpha}\}$ depend on the types and the values of the constraints attached to the node $\phi_\alpha$ and their exact formulation is given in section 2, infra.

When the weighting coefficients $\{v^\alpha(k)\}$ correspond to the harmonic weighting described in section 1.1.4 and in section 2, infra, the weighting functions $f_\alpha^x(\ )$, $f_\alpha^y(\ )$ and $f_\alpha^z(\ )$ may be simplified and take the following form:

The term working memory or working variable refers to any memory area used for storing intermediary results during a computation.

Loading the expression e in a memory m is the operation of evaluating the value of e and storing the result in the memory m. Such an operation is written as follows:

$$m \leftarrow e$$

For any memory m used to store a numerical value, incrementing m by the increment i is the operation of $$\begin{aligned} f_\alpha^x(\ldots) &= \frac{1}{M_\alpha^{*x}} \cdot \Bigg[ \mu(\alpha) \cdot |\Lambda(\alpha)| \cdot \Bigg( \sum_{k \in \Lambda(\alpha)} \phi_k^x \Bigg) - \sum_{k \in \Lambda(\alpha)} \mu(k) \cdot \\ & \quad \Bigg\{ \Bigg( \sum_{\substack{\beta \in \Lambda(k) \\ \beta \neq \alpha}} \phi_\beta^x \Bigg) - |\Lambda(k)| \cdot \phi_k^x \Bigg\} - \sum_i \{\Gamma_i^{x\alpha} - Q_i^{x\alpha}\} \Bigg] \\ f_\alpha^y(\ldots) &= \frac{1}{M_\alpha^{*y}} \cdot \Bigg[ \mu(\alpha) \cdot |\Lambda(\alpha)| \cdot \Bigg( \sum_{k \in \Lambda(\alpha)} \phi_k^y \Bigg) - \sum_{k \in \Lambda(\alpha)} \mu(k) \cdot \\ & \quad \Bigg\{ \Bigg( \sum_{\substack{\beta \in \Lambda(k) \\ \beta \neq \alpha}} \phi_\beta^y \Bigg) - |\Lambda(k)| \cdot \phi_k^y \Bigg\} - \sum_i \{\Gamma_i^{y\alpha} - Q_i^{y\alpha}\} \Bigg] \\ f_\alpha^z(\ldots) &= \frac{1}{M_\alpha^{*z}} \cdot \Bigg[ \mu(\alpha) \cdot |\Lambda(\alpha)| \cdot \Bigg( \sum_{k \in \Lambda(\alpha)} \phi_k^z \Bigg) - \sum_{k \in \Lambda(\alpha)} \mu(k) \cdot \\ & \quad \Bigg\{ \Bigg( \sum_{\substack{\beta \in \Lambda(k) \\ \beta \neq \alpha}} \phi_\beta^z \Bigg) - |\Lambda(k)| \cdot \phi_k^z \Bigg\} - \sum_i \{\Gamma_i^{z\alpha} - Q_i^{z\alpha}\} \Bigg] \end{aligned}$$

$$\text{with:} \begin{cases} M_\alpha^{*x} = M_\alpha + \sum_i \gamma_i^{x\alpha} \\ M_\alpha^{*y} = M_\alpha + \sum_i \gamma_i^{y\alpha} \\ M_\alpha^{*z} = M_\alpha + \sum_i \gamma_i^{z\alpha} \\ M_\alpha = \mu(\alpha) \cdot |\Lambda(\alpha)|^2 + \sum_{k \in \Lambda(\alpha)} \mu(k) \end{cases}$$

Hereafter there is described a method of calculating these functions based on the encoding described in section 1.3.

1.4.2 Notation

In order to simplify the description of the computation process the following notation and definitions are used:

A block of operations is any list of operations beginning with an open curly brace "{" and ending with a closing curly brace "}". The operations in a block may be individual operations or blocks of operations.

computing the value m+i and storing the result in the memory m. Such an operation is written as follows:

$$m \leftarrow m+i$$

In the above operation, the increment i may be:

a constant, or the content of a memory, or an arithmetical expression.

In the above operation, the increment i may be:

a constant, or the content of a memory, or an arithmetical expression.

1.4.3 Fitting process with harmonic weightings

When the coefficients $\{v^\alpha(k)\}$ are the harmonic weightings described in section 1.1.4 and in the appendix, the values $f_\alpha^x$, $f_\alpha^y$ and $f_\alpha^z$ taken by the functions $f_\alpha^x(\ )$, $f_\alpha^y(\ )$ and $f_\alpha^z(\ )$ relating to the node $\vec{\phi}_\alpha$ may be computed efficiently by the following method based on the encoding of S.

0) Allocate the following working memories:

$$\begin{vmatrix} f\alpha^x, f\alpha^y, f\alpha^z \\ \sigma_\phi^x, \sigma_\phi^y, \sigma_\phi^z \\ s_\phi^x, s_\phi^y, s_\phi^z \\ M_\alpha^{-x}, M_\alpha^{-y}, M_\alpha^{-z}, M_\alpha \\ \sigma_\mu \end{vmatrix}$$

1) Perform the following initializations (the order does not matter):

$$\begin{vmatrix} f_\alpha^x = f_\alpha^y = f_\alpha^z = 0 \\ \sigma_\phi^x = \sigma_\phi^y = \sigma_\phi^z = 0 \end{vmatrix}$$

2) Let $n_\alpha$ be the number of satellites of $A(\alpha)$. This number can be obtained from the nb_sat field of $A(\alpha)$.

3) Let $\Lambda(\alpha)$ be the set of the satellites of the atom $A(\alpha)$ accessible from the Sat field of the atom $A(\alpha)$. For each satellite ($k \in \Lambda(\alpha)$, repeat the operations of the following block
{

3.1) Determine the number $n_k$ of satellites of $A(k)$. This number can be obtained from the nb_sat field of $A(k)$.

3.2) Determine the coordinates $(\phi_k^x, \phi_k^y, \phi_k^z)$ of the node $\vec{\phi}_k$ of the atom $A(k)$. These coordinates can be obtained from the Node field of $A(k)$.

3.3) From the data in $A(k)$ calculate or determine the value $\mu(k)$ of the weighting coefficient (see section 1.1.4 and section 2, infra).

3.4) Perform the following operations (in any order):

$$\begin{vmatrix} \sigma_\mu \leftarrow \sigma_\mu + \mu(k) \\ \sigma_\phi^x \leftarrow \sigma_\phi^x + \phi_k^x \\ \sigma_\phi^y \leftarrow \sigma_\phi^y + \phi_k^y \\ \sigma_\phi^z \leftarrow \sigma_\phi^z + \phi_k^z \\ s_\phi^x = s_\phi^y = s_\phi^z = 0 \end{vmatrix}$$

3.5) Let $\Lambda(k)$ be the set of satellites of the atom $A(k)$ accessible from the Sat field of the atom $A(k)$. For each satellite ($\beta \in \Lambda(k)$, $\beta \neq \alpha$) perform the operations of the following block:
{

3.5.2) Determine the current coordinates $(\phi_\beta^x, \phi_\beta^y, \phi_\beta^z)$ of the kernel $\vec{\phi}_\beta$ of the atom $A(\beta)$. These coordinates can be obtained from the Node field of $A(\beta)$.

3.5.3) Perform the following three operations (in any order):

$$\begin{vmatrix} s_\phi^x \leftarrow s_\phi^x + \phi_\beta^x \\ s_\phi^y \leftarrow s_\phi^y + \phi_\beta^y \\ s_\phi^z \leftarrow s_\phi^z + \phi_\beta^z \end{vmatrix}$$

{

3.6) Perform the following three operations (in any order):

$$\begin{vmatrix} f_\alpha^x \leftarrow f_\alpha^x + \mu(k) \times (s_\phi^x - n_k \times \phi_k^x) \\ f_\alpha^y \leftarrow f_\alpha^y + \mu(k) \times (s_\phi^y - n_k \times \phi_k^y) \\ f_\alpha^z \leftarrow f_\alpha^z + \mu(k) \times (s_\phi^z - n_k \times \phi_k^z) \end{vmatrix}$$

}

4) Perform the following operations:

$$\begin{vmatrix} M_\alpha \leftarrow \mu(\alpha) \times n_\alpha \times n_\alpha + \sigma_\mu \\ M_\alpha^{-x} \leftarrow M_\alpha \\ M_\alpha^{-y} \leftarrow M_\alpha \\ M_\alpha^{-z} \leftarrow M_\alpha \end{vmatrix}$$

5) Let $C(\alpha)$ be the set of constraints attached to the atom $A(\alpha)$ that can be accessed by the Const field of this atom. For each constraint ($c \in C(\alpha)$) repeat the operations of the following block:
{

5.1) Determine the type of the constraint c.

5.2) Depending on the type of the constraint c, perform the following two operations:

5.2.1) Extract the data specific to the constraint c.

5.2.2) Depending on the data selected in (5.2.1), compute the values of the following expressions (see sections 2.5 and 2.7, infra):

$$\begin{vmatrix} \Gamma_i^{x\alpha}, & \Gamma_i^{y\alpha}, & \Gamma_i^{z\alpha} \\ Q_i^{x\alpha}, & Q_i^{y\alpha}, & Q_i^{z\alpha} \\ \gamma_i^{x\alpha}, & \gamma_i^{y\alpha}, & \gamma_i^{z\alpha} \end{vmatrix}$$

5.3) Perform the following operations (in any order):

$$\begin{vmatrix} M_\alpha^{-x} \leftarrow M_\alpha^{-x} + \gamma_i^{x\alpha} \\ M_\alpha^{-y} \leftarrow M_\alpha^{-y} + \gamma_i^{y\alpha} \\ M_\alpha^{-z} \leftarrow M_\alpha^{-z} + \gamma_i^{z\alpha} \\ f_\alpha^x \leftarrow f_\alpha^x + (\Gamma_i^{x\alpha} - Q_i^{x\alpha}) \\ f_\alpha^y \leftarrow f_\alpha^y + (\Gamma_i^{y\alpha} - Q_i^{y\alpha}) \\ f_\alpha^z \leftarrow f_\alpha^z + (\Gamma_i^{z\alpha} - Q_i^{z\alpha}) \end{vmatrix}$$

}

6) Perform the following operations (in any order):

$$\begin{vmatrix} f_\alpha^x \leftarrow (\mu(\alpha) \times n_\alpha \times \sigma_\phi^x - f_\alpha^x)/M_\alpha^{-x} \\ f_\alpha^y \leftarrow (\mu(\alpha) \times n_\alpha \times \sigma_\phi^y - f_\alpha^y)/M_\alpha^{-y} \\ f_\alpha^z \leftarrow (\mu(\alpha) \times n_\alpha \times \sigma_\phi^z - f_\alpha^z)/M_\alpha^{-z} \end{vmatrix}$$

At the end of this process, the working memories $f_\alpha^x$, $f_\alpha^y$ and $f_\alpha^z$ contain the values of the functions $f_\alpha^x(\,)$, $f_\alpha^y(\,)$ and $f_\alpha^z(\,)$ used to fit the values of the coordinates of the node $\vec{\phi}_\alpha$:

$$\begin{vmatrix} \phi_\alpha^x \leftarrow f_\alpha^x \\ \phi_\alpha^y \leftarrow f_\alpha^y \\ \phi_\alpha^z \leftarrow f_\alpha^z \end{vmatrix}$$

This fitting process must be applied only to the "free" nodes, that is to say nodes that do not correspond to control nodes (see section 1.1.3).

1.4.4 Variants

Variant 1

The implementation of the fitting method based on the DSI method described in the previous section in the case of harmonic weighting coefficients may be very easily adapted to the case of any other kind of weighting. The general structure of the process remains unchanged, the only changes concerning the incrementing of the working memories allocated at step (0). How these working memories are incremented depends on the weighting adopted.

For example, if the following weighting coefficients $\{v^\alpha(k)\}$ are chosen:

$$v^\alpha(k) = \begin{cases} -1 & \text{if } \alpha = k \\ \frac{1}{|\Lambda(k)|} & \text{if } \alpha \in \Lambda(k) \end{cases}$$

then it is easy to verify that the associated fitting functions are:

$$\begin{vmatrix} f_\alpha^x(\ldots) = \frac{1}{M_\alpha^{*x}} \cdot \left[ \mu(\alpha) \cdot \left( \sum_{k \in \Lambda(\alpha)} \phi_k^x \right) |\Lambda(\alpha)| - \sum_{k \in \Lambda(\alpha)} \mu(k) \cdot \left\{ \left( \sum_{\substack{\beta \in \Lambda(k) \\ \beta \neq \alpha}} \phi_\beta^x \right) |\Lambda(k)|^2 - \phi_k^x |\Lambda(k)| \right\} - \sum_i \{\Gamma_i^{x\alpha} - Q_i^{x\alpha}\} \right] \\ f_\alpha^y(\ldots) = \frac{1}{M_\alpha^{*y}} \cdot \left[ \mu(\alpha) \cdot \left( \sum_{k \in \Lambda(\alpha)} \phi_k^y \right) |\Lambda(\alpha)| - \sum_{k \in \Lambda(\alpha)} \mu(k) \cdot \left\{ \left( \sum_{\substack{\beta \in \Lambda(k) \\ \beta \neq \alpha}} \phi_\beta^y \right) |\Lambda(k)|^2 - \phi_k^y |\Lambda(k)| \right\} - \sum_i \{\Gamma_i^{y\alpha} - Q_i^{y\alpha}\} \right] \\ f_\alpha^z(\ldots) = \frac{1}{M_\alpha^{*z}} \cdot \left[ \mu(\alpha) \cdot \left( \sum_{k \in \Lambda(\alpha)} \phi_k^z \right) |\Lambda(\alpha)| - \sum_{k \in \Lambda(\alpha)} \mu(k) \cdot \left\{ \left( \sum_{\substack{\beta \in \Lambda(k) \\ \beta \neq \alpha}} \phi_\beta^z \right) |\Lambda(k)|^2 - \phi_k^z |\Lambda(k)| \right\} - \sum_i \{\Gamma_i^{z\alpha} - Q_i^{z\alpha}\} \right] \end{vmatrix}$$

with:
$$\begin{cases} M_\alpha^{*x} = M_\alpha + \sum_i \gamma_i^{x\alpha} \\ M_\alpha^{*y} = M_\alpha + \sum_i \gamma_i^{y\alpha} \\ M_\alpha^{*z} = M_\alpha + \sum_i \gamma_i^{z\alpha} \\ M_\alpha = \mu(\alpha) + \sum_{k \in \Lambda(\alpha)} \{\mu(k)/|\Lambda(k)|^2\} \end{cases}$$

The process used to compute the values $f_\alpha^x$, $f_\alpha^y$ and $f_\alpha^z$ of these functions at node $\vec{\phi}_\alpha$ is then almost identical to the process described for harmonic weighting:

0) Allocate the following working memories:

$$\begin{vmatrix} f_\alpha^x, f_\alpha^y, f_\alpha^z \\ \sigma_\phi^x, \sigma_\phi^y, \sigma_\phi^z \\ s_\phi^x, s_\phi^y, s_\phi^z \\ M_\alpha^{-x}, M_\alpha^{-y}, M_\alpha^{-z}, M_\alpha \\ \sigma_\mu, n_k^2 \end{vmatrix}$$

1) Perform the following initializations (the order does not matter):

$$\begin{vmatrix} f_\alpha^x = f_\alpha^y = f_\alpha^z = 0 \\ \sigma_\phi^x = \sigma_\phi^y = \sigma_\phi^z = 0 \end{vmatrix}$$

2) Determine the number $n_\alpha$ of satellites of $A(\alpha)$. This number can be obtained from the nb_sat field of $A(\alpha)$ 3) Let $\Lambda(\alpha)$ be the set of satellites of the atom $A(\alpha)$ accessible from the Sat field of the atom $A(\alpha)$. For each satellite ($k\epsilon\Lambda(\alpha)$) repeat the operations of the following block:
{
3.1) Determine the number $n_k$ of satellites of $A(k)$. This number can be obtained from the nb_sat field of $A(k)$. Then perform the following operation:

$$n_k^2 \leftarrow n_k \times n_k$$

3.2) Determine the coordinates $(\phi_k^x, \phi_k^y, \phi_k^z)$ of the Node $\vec{\phi}_k$ of the atom $A(k)$. These coordinates can be obtained from the Node field of $A(k)$.

3.3) From the data in $A(k)$ calculate or determine the value $\mu(k)$ of the weighting coefficient (see section 1.1.4 and section 2, infra).

3.4) Perform the following operations (in any order):

$$\begin{vmatrix} \sigma_\mu \leftarrow \sigma_\mu + \mu(k)/n_k^2 \\ \sigma_\phi^x \leftarrow \sigma_\phi^x + \phi_k^x \\ \sigma_\phi^y \leftarrow \sigma_\phi^y + \phi_k^y \\ \sigma_\phi^z \leftarrow \sigma_\phi^z + \phi_k^z \\ s_\phi^x = s_\phi^y = s_\phi^z = 0 \end{vmatrix}$$

3.5) Let $\Lambda(k)$ be the set of satellites of the atom $A(k)$ accessible from the Sat field of the atom $A(k)$. For each satellite $\beta\epsilon\Lambda(k)$, $\beta\neq\alpha$ perform the operations of the following block:
{
3.5.2) Determine the current coordinates $(\phi_\beta^x, \phi_\beta^y, \phi_\beta^z)$ of the kernel $\vec{\phi}_\beta$ of the atom $A(\beta)$. These coordinates can be obtained from the Node field of $A(\beta)$.

3.5.3) Perform the following three operations (in any order):

$$\begin{vmatrix} s_\phi^x \leftarrow s_\phi^x + \phi_\beta^x \\ s_\phi^y \leftarrow s_\phi^y + \phi_\beta^y \\ s_\phi^z \leftarrow s_\phi^z + \phi_\beta^z \end{vmatrix}$$

}
3.6) Perform the following three operations (in any order):

$$\begin{vmatrix} f_\alpha^x \leftarrow f_\alpha^x + \mu(k) \times (s_\phi^x/n_k^2 - \phi_k^x/n_k) \\ f_\alpha^y \leftarrow f_\alpha^y + \mu(k) \times (s_\phi^y/n_k^2 - \phi_k^y/n_k) \\ f_\alpha^z \leftarrow f_\alpha^z + \mu(k) \times (s_\phi^z/n_k^2 - \phi_k^z/n_k) \end{vmatrix}$$

}

4) Perform the following operations:

$$\begin{vmatrix} M_\alpha \leftarrow \mu(\alpha) + \sigma_\mu \\ M_\alpha^{-x} \leftarrow M_\alpha \\ M_\alpha^{-y} \leftarrow M_\alpha \\ M_\alpha^{-z} \leftarrow M_\alpha \end{vmatrix}$$

5) Let $C(\alpha)$ be the set of constraints attached to the atom $A(\alpha)$ accessed by the Const field of this atom. For each constraint $c\epsilon C(\alpha)$ repeat the operations of the following block:
{
5.1) Determine the type of the constraint c.
5.2) Depending on the type of the constraint c, perform the following two operations:
5.2.1) Extract the data specific to the constraint c.
5.2.2) Depending on the data selected in (5.2.1), compute the values of the following expressions (see sections 2.5 and 2.7, infra):

$$\begin{vmatrix} \Gamma_i^{x\alpha}, \Gamma_i^{y\alpha}, \Gamma_i^{z\alpha} \\ Q_i^{x\alpha}, Q_i^{y\alpha}, Q_i^{z\alpha} \\ \gamma_i^{x\alpha}, \gamma_i^{y\alpha}, \gamma_i^{z\alpha} \end{vmatrix}$$

5.3) Perform the following operations (in any order):

$$\begin{vmatrix} M_\alpha^{-x} \leftarrow M_\alpha^{-x} + \gamma_i^{x\alpha} \\ M_\alpha^{-y} \leftarrow M_\alpha^{-y} + \gamma_i^{y\alpha} \\ M_\alpha^{-z} \leftarrow M_\alpha^{-z} + \gamma_i^{z\alpha} \\ f_\alpha^x \leftarrow f_\alpha^x + (\Gamma_i^{x\alpha} - Q_i^{x\alpha}) \\ f_\alpha^y \leftarrow f_\alpha^y + (\Gamma_i^{y\alpha} - Q_i^{y\alpha}) \\ f_\alpha^z \leftarrow f_\alpha^z + (\Gamma_i^{z\alpha} - Q_i^{z\alpha}) \end{vmatrix}$$

}
6) Perform the following operations (in any order):

$$\begin{vmatrix} f_\alpha^x \leftarrow (\mu(\alpha) \times \sigma_\phi^x/n_\alpha - f_\alpha^x)/M_\alpha^{-x} \\ f_\alpha^y \leftarrow (\mu(\alpha) \times \sigma_\phi^y/n_\alpha - f_\alpha^y)/M_\alpha^{-y} \\ f_\alpha^z \leftarrow (\mu(\alpha) \times \sigma_\phi^z/n_\alpha - f_\alpha^z)/M_\alpha^{-z} \end{vmatrix}$$

The numerical parameters stored in the Info field of the atoms may be interpolated by the DSI method (see appendix: sections 2.1.2 and 2.2, infra). In this case, the process is almost identical to the process described above used to fit a surface; the only modification consists in using only one of the three functions normally dedicated to fitting the three coordinates of the nodes and to calculate it according to the interpolated parameter.

The present invention finds applications in the following fields in particular:
  in geology and in geophysics, it can be used to create a surface model, for example to construct a solid three-dimensional model, on which a geophysical simulation or an underground resources exploitation simulation can be carried out; it can also be used to obtain a set of data for initializing a digital or analogue simulator of geophysical or resource exploitation phenomena; it can further be used, in conjuction with a graphics workstation, to display on a screen or to print out on paper images used to monitor simulations as above;

in biology or in medicine, the invention can be used to construct three-dimensional models of organs and/or prostheses or to simulate the effects of plastic surgery; similarly, displayed or printed two-dimensional images can be used to monitor the above operations.

However, it is obvious that the invention applies more generally to modeling surfaces of any kind and in particular any natural or man-made surface. It can be of particular benefit in computer-aided design (CAD).

Finally, the present invention is in no way limited to the embodiment described above and shown in the drawings and those skilled in the art can vary and modify the embodiment as described above without departing from the scope of the invention.

NEW VERSION OF THE DSI METHOD FOR INTERACTIVE MODELING OF COMPLEX SURFACES

In Geology and Biology, a common problem is modeling complex surfaces such as interfaces between areas of different kinds or having different properties. Classical modeling techniques based on Bézier interpolations and spline functions [9] are not well suited to processing this type of heterogeneous data. A different approach is based on the DSI ("Discrete Smooth Interpolation") method [8]. In this approach, surfaces are modeled using irregular triangular facets whose vertices must be determined to allow for the largest possible quantities of heterogeneous data.

Figure 12:
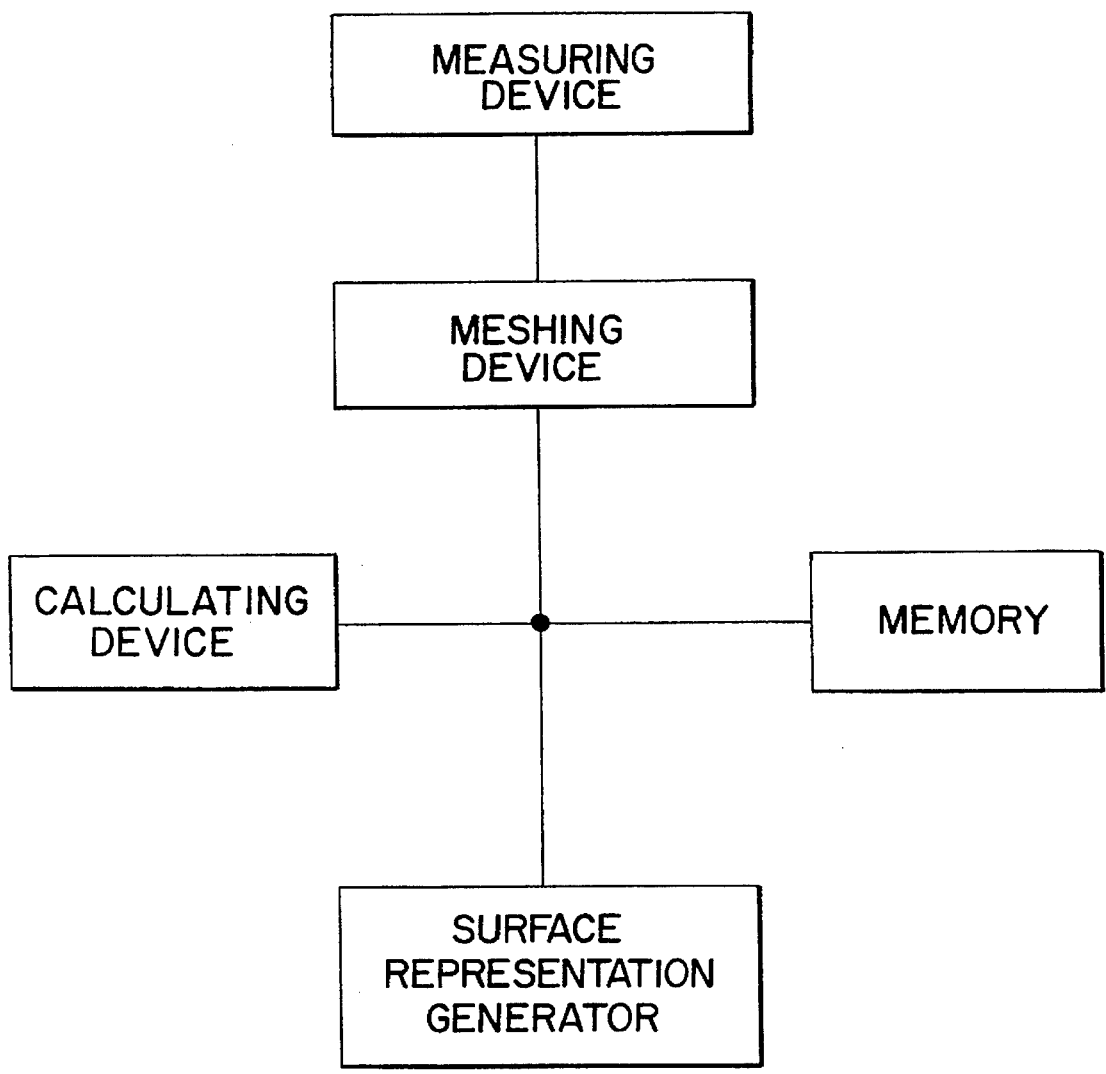
FIG. 12 shows an apparatus embodiment of the present invention.

FIG. 12 shows an apparatus according to the present invention, which can be utilized to implement the different surface modelling methods of the present invention. The surface modelling apparatus, as exemplified in FIG. 12, comprises a measuring device which measures to obtain a set of geometrical data, a meshing device which meshes a surface to be modelled, a memory to store data related to and for each mode of the mesh, a calculating device which processes fitting of the surface according to the stored data, and a surface representation generator for creating a representation of the surface from fitted coordinates of each node.

2.1 Introduction: Statement of the problem

2.1.1 Surface S and related definitions

Referring to FIG. 1, let S be a surface composed of contiguous flat triangular facets embedded in the 3D Euclidian space (O|x,y,z). This surface need not be connex or closed. The following notation is used:

$$\begin{cases} G = G(S) = \text{set of the edges of the triangles,} \\ \Omega = \Omega(S) = \text{set of the apices of the triangles,} \\ N = |\Omega| = \text{number of points in } \Omega. \end{cases}$$

G is a graph whose nodes are the points of $\Omega$ and this set $\Omega$ is identified with the set of integer indices $\{1, \ldots, N\}$ used to number the nodes. The neighborhood $N(k)$ of a node $k \in \Omega$ iS defined as:

$$N(k) = \text{subset of } \Omega \text{ constituted by the nodes of } \Omega \text{ that can be reached from node } k \text{ in at most } s(k) \text{ steps where } s(k) \text{ is a given positive number.}$$

In the following, it is assumed that these neighborhoods $N(k)$ have the following symmetry property:

$$\alpha \in N(\beta) \iff \beta \in N(\alpha)$$

The neighborhoods $N(k)$ so defined thus generate a topology on G that can be considered as an approximate topology for S itself.

2.1.2 Problem 1: Estimating a function $\phi$ defined on $\Omega$

Assume that the position of each node $k \in \Omega$ iS known and let $\phi(k)$ be a function defined for all nodes $k \in \Omega$ and known only on a subset of $\Omega$:

$$\begin{cases} L = \text{set of nodes } l \in \Omega \text{ where } \phi(l) = \phi_l \text{ is known,} \\ I = \text{set of nodes } i \in \Omega \text{ where } \phi(i) = \phi_i \text{ is unknown,} \\ = \Omega - L. \end{cases}$$

Generally, L is different from $\Omega$ and there is an infinity of functions $\phi(k)$ defined on $\Omega$ and interpolating the values $\{\phi(l)=\phi_l : l \in L\}$. The goal is to select among all such functions the one which minimizes a given criterion $R^*(\phi)$ measuring:

the global roughness of the function $\phi(.)$, the discrepancy between the function $\phi(.)$ and some constraints and data that it should satisfy.

2.1.3 Problem 2: Fitting the surface S

In this case, only a subset of L of nodes $k \in \Omega$ have a known position $\vec{\phi}(k) = \vec{\phi}_k$.

$$\begin{cases} L = \text{set of nodes } l \in \Omega \text{ where } \phi(l) = \phi_l \text{ is known,} \\ I = \text{set of nodes } i \in \Omega \text{ where } \phi(i) = \phi_i \text{ is unknown,} \\ = \Omega - L. \end{cases}$$

As for the first problem, L is generally different from $\Omega$ and there is an infinity of surfaces S interpolating the points $\{\vec{\phi}(l)=\phi_l : l \in L\}$. The goal is to select among all such surfaces the one which minimizes a given criterion $R^*(\vec{\phi})$ measuring:

the global roughness of the surface S, the discrepancy between the surface S and some constraints and data that it must satisfy.

Allowing for the independence of the components $(\phi^x(k), \phi^y(k), \phi^z(k))$ of each vector $\vec{\phi}(k)$, it is easy to use the solution of the first problem to solve the second by simply writing:

$$R^*(\vec{\phi}) = R^*(\phi^x) + R(\phi^y) + R^*(\phi^z)$$

In the very particular case where the set $\Omega$ corresponds to the nodes of a regular rectangular grid laid on the surface, consideration might be given to using a Bézier, spline or Briggs type interpolation method (See [9], [1] and [3]); unfortunately these methods are not appropriate for irregular grids and cannot allow for the constraints described in sections 2.2.3, 2.5 and 2.7.2.

2.2 Interpolating a function $\phi(k)$ defined on $\Omega$

This section briefly introduces the Discrete Smooth Interpolation method described in [8].

2.2.1 Notation

In the following, $\phi$ denotes a column matrix of size N as:

$$\left| \begin{array}{rcl} \phi & = & [\phi_1, \ldots, \phi_N]^t \\ \phi_k & = & \phi(k) \quad k\in\Omega \end{array} \right.$$

The problem does not depend on the method of numbering the nodes of the grid. In order to simplify the notation, it will therefore be assumed that a permutation of the elements of the matrix $\phi$ has been performed in such a way that $\phi$ can be split into two submatrices $\phi_I$ and $\phi_L$ such that:

$$\phi = \begin{bmatrix} \phi_I \\ \phi_L \end{bmatrix} \Longleftrightarrow \begin{cases} \phi_I = \begin{bmatrix} \phi_{i_1} \\ \vdots \\ \phi_{i_n} \end{bmatrix} & \text{with } i_\alpha \in I \quad \alpha \\ \phi_L = \begin{bmatrix} \phi_{l_1} \\ \vdots \\ \phi_{l_m} \end{bmatrix} & \text{with } l_\beta \in L \quad \beta \end{cases}$$

Moreover, $\|.\|_D$ denotes a seminorm associated to a square (N×N) positive semidefinite matrix [D] in such a way that, for any column matrix X of size N:

$$\|X\|_D^2 = X^t \cdot [D] \cdot X$$

2.2.2 Defining a global roughness criterion $R(\phi)$

Let $R(\phi|k)$ be a local roughness criterion defined by the following formula where $\{v^\alpha(k)\}$ are given positive, negative or null weighting coefficients:

$$R(\phi|k) = \left| \sum_{\alpha \in N(k)} v^\alpha(k) \cdot \phi_\alpha \right|^2$$

$R(\phi|k)$ can be used to derive a global roughness criterion $R(\phi)$ defined as follows, where $\mu(k)$ is a given weighting function defined on $\Omega$:

$$R(\phi) = k\Sigma \, \mu(k) \cdot R(\phi|k)$$

$R(\phi)$ is completely defined by the coefficients $\{v^\alpha(k)\}$ and $\mu(k)$ and it is easy to verify (See [8]) that there is always an (N×N) symmetric positive semidefinite matrix [W] such that:

$$R(\phi|k) = \phi^t \cdot [W(k)] \cdot \phi$$

2.2.3 Allowing for linear constraints in a least squares sense

Consider a square (N×N) matrix $[A_i]$ and an N column matrix $B_i$ defining the linear constraint:

$$[A_i] \cdot \phi \simeq B_i$$

For an N×N positive semidefinite matrix $[D_i]$ "$\simeq$" means:

$$\|[A_i]\cdot\phi - B_i\|_{D_i}^2 \text{ as small as possible}$$

If there are several conditions of this type, the degree of violation of these constraints can be measured by the criterion $\rho(\phi)$ with:

$$\rho(\phi) = i\Sigma \, \|[A_i] \cdot \phi - B_i\|^{2D_i}$$

2.2.4 Solution of the problem

Among all the functions $\phi(k)$ defined on $\Omega$ and interpolating the data $\{\phi(I)=\phi_I : I\in L\}$, one is selected which minimizes the following criterion:

$$R^*(\phi) = R(\phi) + \rho(\phi)$$

Developing $R^*(\phi)$:

$$\left| \begin{array}{l} R^*(\phi) = \phi^t \cdot [W^*] \cdot \phi - 2 \cdot \phi^t \cdot [Q] + C \\ \text{with} \begin{cases} [W^*] = \sum_i [A_i]^t \cdot [D_i] \cdot [A_i] + [W] \\ Q = \sum_i [A_i]^t \cdot [D_i] \cdot B_i \\ C = \sum_i B_{iD_i}^2 \end{cases} \end{array} \right.$$

The partition of the matrix $\phi$ induces a similar partition of the matrices $[W^*]$ and Q used to define $R^*(\phi)$:

$$\phi = \begin{bmatrix} \phi_I \\ \phi_L \end{bmatrix} \longrightarrow [W^*] = \begin{bmatrix} W_{II}^* & W_{IL}^* \\ W_{LI}^* & W_{LL}^* \end{bmatrix};$$

$$Q = \begin{bmatrix} Q_I \\ Q_L \end{bmatrix}$$

The condition $\partial R^*(\phi)/\partial_{100_i} = [0]$ yields the following "DSI equation" characterizing all the functions $\{\phi(k):k\in\Omega\}$ constituting a solution of the problem:

$$(DSI): \begin{cases} [W_{II}^*] \cdot \phi_I = \psi_I \\ \text{with: } \psi_I = -[W_{IL}^*] \cdot \phi_L + Q_I \end{cases}$$

2.3 Uniqueness of the solution of the DSI equation

Definition

The set L of nodes where $\phi$ is known is said to be consistent relative to $R^*(\phi)$ if each connex component of the graph G contains at least one node belonging to L.

Theorem

If the global roughness criterion $R(\phi)$ is such that:

$$\left| \begin{array}{ll} 1) \, L & \text{is consistent relative to } R(\phi) \\ 2) \, \mu(k) & > 0 \quad k \\ 3) \, v^\alpha(k) & \geq 0 \quad \{\alpha \neq k, \alpha \in N(k)\} \\ 4) \, v^k(k) & \leq -\sum_{\substack{\alpha \in N(k) \\ \alpha \neq k}} v^\alpha(k) \neq 0 \end{array} \right.$$

the DSI equation based on $R(\phi)$ has a unique solution.

Proof

The theorem explained above is of theoretical interest only and does not affect in any way the method described in this patent. It therefore requires no proof here.

2.4 Local form of the DSI equation

In the following, instead of solving directly the DSI matrix equation, an iterative approach avoids the computation and storage of [W*]. This iterative approach is that used in this patent.

In order to simplify the notation, it will be assumed in the following that the positive semi-definite matrices [Di] of the DSI equation are diagonal. Moreover, when linear constraints of the type $[A_i] \cdot \phi = B_i$ exist, the following notation is used:

$$\begin{bmatrix} A_i^{kh} = \text{element of } [Ai] \text{ located on } \begin{cases} \text{row} & k \\ \text{column} & h \end{cases} \\ Q_i^{\alpha} = \alpha^{th} \text{ element of the column matrix } ([A_i]^t [Di] B_i) \end{bmatrix}$$

2.4.1 Computing $\partial R^*(\phi)/\partial_{\phi_\alpha}$

The definition of $R(\phi|k)$ implies:

$$R(\phi|k) = \sum_{\beta \in N(k)} \sum_{\gamma \in N(k)} v^\beta(k) v^\gamma(k) \cdot \phi_\beta \phi_\gamma$$
$$= \sum_{\beta \in N(k)} (v^\beta(k))^2 \cdot \phi_\beta^2 +$$
$$\sum_{\gamma \in N(k)} \sum_{\substack{\beta \in N(k) \\ \beta \neq \gamma}} v^\beta(k) v^\gamma(k) \cdot \phi_\beta \phi_\gamma$$

$$\implies \frac{\partial R(\phi|k)}{\partial \phi_\alpha} =$$

$$\begin{cases} 2 \cdot (v^\alpha(k))^2 \cdot \phi_\alpha + 2 \cdot v^\alpha(k) \cdot \sum_{\substack{\beta \in N(k) \\ \beta \neq \alpha}} v^\beta(k) \cdot \phi_\beta & \text{if } \alpha \in N(k) \\ 0 & \text{else} \end{cases}$$

From this it can be deduced that:

$$\frac{1}{2} \cdot \frac{\partial R(\phi)}{\partial \phi_\alpha} = \frac{1}{2} \sum_k \mu(k) \cdot \frac{\partial R(\phi|k)}{\partial \phi_\alpha} =$$

$$\frac{1}{2} \sum_{k \in N(\alpha)} \mu(k) \cdot \frac{\partial R(\phi|k)}{\partial \phi_\alpha} = \phi_\alpha \cdot \sum_{k \in N(\alpha)} \mu(k) (v^\alpha(k))^2 +$$

$$\sum_{k \in N(\alpha)} \left\{ \mu(k) v^\alpha(k) \cdot \sum_{\substack{\beta \in N(k) \\ \beta \neq \alpha}} v^\beta(k) \cdot \phi_\beta \right\}$$

Allowing for the diagonal structure of [Di], it is easy to verify that the $\alpha^{th}$ element of $\partial \|[A_i] \cdot \phi - B_i\|_{D_i}^2 / \partial_{\phi_\alpha}$ is such that:

$$\frac{1}{2} \cdot \frac{\partial \|[A_i] \cdot \phi - B_i\|_{D_i}^2}{\partial \phi_\alpha} = \sum_k \left\{ A_i^{k\alpha} D_i^{kk} \cdot \sum_\beta A_i^{k\beta} \phi_\beta \right\} -$$

$$Q_i^\alpha = \phi_\alpha \cdot \sum_k D_i^{kk} (A_i^{k\alpha})^2 + \sum_k \left\{ A_i^{k\alpha} D_i^{kk} \cdot \sum_{\substack{\beta \neq \alpha}} A_i^{k\beta} \phi_\beta \right\} - Q_i^\alpha$$

Given the definition of $R^*(\phi)$, it is possible to deduce that:

$$\frac{1}{2} \cdot \frac{R^*(\phi)}{\partial \phi_\alpha} = \phi_\alpha \cdot$$

$$\left\{ \sum_{k \in N(\alpha)} \mu(k) (v^\alpha(k))^2 + \sum_i \sum_k D_i^{kk} (A_i^{k\alpha})^2 \right\} +$$

$$\left\{ \sum_{k \in N(\alpha)} \mu(k) v^\alpha(k) \cdot \sum_{\substack{\beta \in N(k) \\ \beta \neq \alpha}} v^\beta(k) \cdot \phi_\beta \right\} +$$

$$\sum_i \sum_k \left\{ A_i^{k\alpha} D_i^{kk} \cdot \sum_{\substack{\beta \neq \alpha}} A_i^{k\beta} \phi_\beta \right\} - \sum_i Q_i^\alpha$$

The solution $\phi$ is such that $\partial R^*(\phi)/\partial_{\phi_\alpha} = 0$, hence the $\alpha^{th}$ component $\phi_\alpha$ of $\phi$ must satisfy the following equation:

$DSI(\alpha)$:

$$\begin{bmatrix} \phi_\alpha = -\frac{1}{M_\alpha^*} \cdot \left\{ \sum_{k \in N(\alpha)} \left\{ \mu(k) v^\alpha(k) \cdot \sum_{\substack{\beta \in N(k) \\ \beta \neq \alpha}} v^\beta(k) \phi_\beta \right\} + \sum_i \{\Gamma_i^\alpha - Q_i^\alpha\} \right\} \\ \text{with:} \begin{cases} M_\alpha^* = M_\alpha + \sum_i \gamma_i^\alpha \\ M_\alpha = \sum_{k \in N(\alpha)} \mu(k)(v^\alpha(k))^2 \\ \gamma_i^\alpha = \sum_k D_i^{kk}(A_i^{k\alpha})^2 \\ \Gamma_i^\alpha = \sum_k \left\{ A_i^{k\alpha} D_i^{kk} \cdot \sum_{\beta \neq \alpha} A_i^{k\beta} \phi_\beta \right\} \\ Q_i^\alpha = \sum_k A_i^{k\alpha} D_i^{kk} B_i^k \end{cases} \end{bmatrix}$$

In this disclosure this equation is called the local form of the DSI equation at node $\alpha$.

2.4.2 Proposition for an iterative algorithm

The above local form of the DSI equation suggests a straightforward algorithm to estimate the solution $\phi$. For example, at iteration (n+1) the $\alpha^{th}$ component $\phi_\alpha^{(n+1)}$ of the solution $\phi^{(n+1)}$ must satisfy the DSI($\alpha$) equation so that an iterative algorithm can be:

let $I$ be the set of indexes of nodes where $\phi_\alpha$ is unknown,
let $\phi$ be an initial approximate solution,
while (more iterations are needed).

```
{
for_all(α∈I)
    {
    M_α* = {...}
    φ_α = - 1/M_α* · {...}
    }
}
```

Note that this very simple algorithm does not use explicitly the matrix [W*] occurring in the DSI equation but has to compute repeatedly products such as $\{v^\alpha(k) \cdot v^\beta(k)\}$ which are the products used to derive [W].

In fact, if the initial approximate solution is close to the exact solution, few iterations are needed and the computation overhead becomes negligible. For example, this occurs in an interactive context where the initial solution $\phi$ is taken equal to the solution before some local modifications are made by the user. In this case, despite the slight increase in overhead, the local form of the DSI equation is preferable as it is much easier to use than the global form.

In order to show that the proposed algorithm actually converges, note that $R^*(\phi)$ can be expressed as a function of $\phi_\alpha$:

$$R^*(\phi) = A \cdot \phi_\alpha^2 + B \cdot \phi_\alpha + C$$

The coefficients A, B and C are independent of $\phi_\alpha$ and:

$$\begin{cases} A = \sum_{k \in N(\alpha)} \mu(k)(v^\alpha(k))^2 + \sum_i \gamma_i^\alpha \\ B = 2 \cdot \left\{ \sum_{k \in N(\alpha)} \left\{ \mu(k) v^\alpha(k) \cdot \sum_{\substack{\beta \in N(k) \\ \beta \neq \alpha}} v^\beta(k) \cdot \phi_\beta \right\} + \sum_i \{\Gamma_i^\alpha - Q_i^\alpha\} \right\} \end{cases}$$

The minimum of the global criterion $R^*(\phi)$ is achieved for the value $\phi_\alpha = -B/(2A)$ which is precisely the value given by the DSI($\alpha$) equation. This shows that the algorithm converges because, at each step of the iterative process, the value of the positive or null function $R^*(\phi)$ decreases.

2.5 Allowing for fuzzy data

This section introduces two types of linear constraints that will be of special importance for Geometric Modeling, as will be shown in section 2.7.6. The purpose of this section is to account for fuzzy data concerning the unknown values $\{\phi_\lambda : \lambda \in I\}$. Such data is assumed to be associated with certainty factors $\omega^2 \in R^+$ which are actually positive weighting coefficients.

2.5.1 Case of isolated fuzzy data

Let $\lambda \in I$ be a node index for which the unknown value $\phi\lambda$ is assumed to be close to an uncertain datum $\tilde{\phi}\lambda$ with a certainty factor equal to $\omega_\lambda^2$.

$$\phi_\lambda \simeq \tilde{\phi}_\lambda$$

where $\simeq$ represents the following condition: $\phi\lambda$:

$$\omega_\lambda^2 \cdot |\phi_\lambda^* - \tilde{\phi}_\lambda|^2 \text{ minimum}$$

Such a condition is easily accounted for in the DSI method as the $i^{th}$ constraint with:

$$A_i^{kh} = \begin{cases} +1 & \text{if } k = h = \lambda \\ 0 & \text{else} \end{cases}$$

$$B_i^k = \begin{cases} \tilde{\phi}_\lambda & \text{if } k = \lambda \\ 0 & \text{else} \end{cases}$$

and $$D_i^{kh} = \begin{cases} \omega_\lambda^2 & \text{if } k = h = \lambda \\ 0 & \text{else} \end{cases}$$

The corresponding coefficients $\Gamma_i^\alpha$, $Q_i^\alpha$ and $\gamma_i^\alpha$ used in the local DSI($\alpha$) equation are thus defined by:

$$\Gamma_i^\alpha = 0$$

$$Q_i^\alpha = \begin{cases} \omega_\lambda^2 \cdot \tilde{\phi}_\lambda & \text{if } \alpha = \lambda \\ 0 & \text{else} \end{cases}$$

and $$\gamma_i^\alpha = \begin{cases} \omega_\lambda^2 & \text{if } \alpha = \lambda \\ 0 & \text{else} \end{cases}$$

2.5.2 Case of differential fuzzy data

Let $\lambda \in I$ be a node index for which the unknown value $\phi\lambda$ is assumed to be linked to another value $\phi\mu$ corresponding to another index $\mu \neq \lambda$. Assume that this link is of the following form, where $\Delta_{\lambda\mu}$ is a given value:

$$(\phi_\mu - \phi_\lambda) \simeq \Delta_{\lambda\mu}$$

This relation is assumed to be fuzzy and is modeled through the following condition involving a certainty factor $\omega_{\lambda\mu}^2$:

$$\omega_{\lambda\mu}^2 \cdot |(\phi_\mu^* - \phi_\lambda^*) - \Delta_{\lambda\mu}|^2 \text{ minimum}$$

Such a condition can easily be accounted for in the DSI method as the $i^{th}$ constraint with:

$$A_i^{kh} = \begin{cases} -1 & \text{if } k = h = \lambda \\ -1 & \text{if } k = h = \mu \\ +1 & \text{if } k = \lambda \text{ and } h = \mu \\ +1 & \text{if } k = \mu \text{ and } h = \lambda \\ 0 & \text{else} \end{cases}$$

$$B_i^k = \begin{cases} + \Delta_{\lambda\mu} & \text{if } k = \lambda \\ - \Delta_{\lambda\mu} & \text{if } k = \mu \\ 0 & \text{else} \end{cases}$$

-continued and $$D_i^{kh} = \begin{cases} \frac{1}{2} \omega_{\lambda_\mu}^2 & \text{if } k=h=\lambda \\ \frac{1}{2} \omega_{\lambda_\mu}^2 & \text{if } k=h=\mu \\ 0 & \text{else} \end{cases}$$

The corresponding coefficients $\Gamma_i^\alpha$, $Q_i^\alpha$ and $\gamma_i^\alpha$ used in the DSI($\alpha$) equation are thus defined by:

$$\Gamma_i^\alpha = \begin{cases} -\omega_{\lambda\mu}^2 \cdot \phi_\mu^* & \text{if } \alpha = \lambda \\ -\omega_{\lambda\mu}^2 \cdot \phi_\lambda^* & \text{if } \alpha = \mu \\ 0 & \text{else} \end{cases}$$

$$Q_i^\alpha = \begin{cases} -\omega_{\lambda\mu}^2 \cdot \Delta_{\lambda\mu} & \text{if } \alpha = \lambda \\ +\omega_{\lambda\mu}^2 \cdot \Delta_{\lambda\mu} & \text{if } \alpha = \mu \\ 0 & \text{else} \end{cases}$$

and $$\gamma_i^\alpha = \begin{cases} \omega_{\lambda\mu}^2 & \text{if } \alpha = \lambda \\ \omega_{\lambda\mu}^2 & \text{if } \alpha = \mu \\ 0 & \text{else} \end{cases}$$

2.5.3 Choosing the certainty factors $$DSI(\alpha): \begin{bmatrix} \phi_\alpha = \frac{1}{M_\alpha^*} \left[ \mu(\alpha) \cdot |\Lambda(\alpha)| \cdot \left( \sum_{\beta \in \Lambda(\alpha)} \phi_\beta \right) - \sum_{k \in \Lambda(\alpha)} \mu(k) \cdot \left\{ \left( \sum_{\substack{\beta \in \Lambda(k) \\ \beta \neq \alpha}} \phi_\beta \right) - |\Lambda(k)| \cdot \phi_k \right\} - \sum_i \{\Gamma_i^\alpha - Q_i^\alpha\} \right] \\ \text{with: } M_\alpha^* = \mu(\alpha) \cdot |\Lambda(\alpha)|^2 + \sum_{k \in \Lambda(\alpha)} \mu(k) + \sum_i \gamma_i^\alpha \end{bmatrix}$$

Consider the term $M_\alpha^*$ of the DSI($\alpha$) equation:

$$\begin{bmatrix} M_\alpha^* = M_\alpha + \gamma_1^\alpha + \gamma_2^\alpha + \ldots \\ \text{with: } M_\alpha = \sum_{k \in N(\alpha)} \mu(k) \, (\upsilon^\alpha(k))^2 \end{bmatrix}$$

In the two examples discussed above, the terms $\gamma_1^\alpha$ are either equal to zero or equal to the certainty factor:

$$\gamma_i^\alpha = \omega_i^2$$

This suggests choosing for $\omega_i^2$ a given percentage $P_i$ of $M_\alpha$:

$$\omega_i^2 = p_i \cdot M_\alpha \quad p_i > 0$$

The term $M_\alpha^*$ of the DSI($\alpha$) equation is then:

$$M_\alpha^* = M_\alpha \cdot (1 + p_1(\alpha) + p_2(\alpha) + \ldots)$$

where $p_i(\alpha)$ is either equal to a given percentage $P_i$ or equal to zero.

2.6 Choosing the weighting coefficients

The choice of the weighting coefficients $\{v^\alpha(k)\}$ and $\{\mu(k)\}$ is completely free except that the $\{\mu(k)\}$ coefficients have to be positive or equal to zero. In the following an example is given of how to choose these two families of coefficients.

2.6.1 Choosing the $\{v^\alpha(k)\}$ harmonic weighting coefficients

Let $\Lambda(k)$ be the "orbit" of k defined as follows:

$$\Lambda(k) = N(k) - \{k\}$$

Let $|\Lambda(k)|$ be the number of elements of (k). The weighting is called harmonic weighting if the coefficients $\{v^\alpha(k)\}$ are chosen according to the following definition:

$$\upsilon^\alpha(k) = \begin{cases} -|\Lambda(k)| & \text{if } \alpha = k \\ 1 & \text{if } \alpha \in \Lambda(k) \end{cases}$$

Harmonic functions have the characteristic property that they are equal at any point to their own mean on a circle centered on this point. As one can see, $R(\phi|k)=0$ if $\phi_k$ is equal to the mean of the values $\phi_\alpha$ surrounding the node k, this is why, by analogy with harmonic functions, the term harmonic has been adopted for the weighting coefficients $\{v^\alpha(k)\}$ described in this section.

If the DSI($\alpha$) equation is developed with these coefficients, the following equation is obtained, which can be easily translated into programming language:

2.6.2 Choosing the $\{\mu(k)\}$ coefficients

The coefficients $\{\mu(k)\}$ have been introduced in order to modulate locally the smoothness of the interpolation. If there is no special reason to do differently, a uniform weighting may be used:

$$\mu(k) = 1 \,\forall k \in \Omega$$

Among all non-uniform weighting schemes, one seems to be particularly interesting if smoothness is needed in the neighborhood of the data:

$$\mu(k) = \begin{cases} 1 & \text{if } k \in I \\ m > 1 & \text{if } k \in L \end{cases}$$

2.7 Application to Geometric Modeling

This section shows how to use the DSI method to estimate the triangulated surface S itself for which it will be assumed that partial data is available composed of:

the exact location of some apices of the triangles,
the approximate location of some apices of the triangles,
vectorial constraints specifying the shape of S,
etc.

To this end, $\vec{\phi}_\alpha$ is defined as the current vector joining the origin of $R^3$ to the current node of $\Omega$ and $\phi^x$, $\phi^y$ and $\phi^z$ denote its components on the $\{\vec{ox}, \vec{oy}, \vec{oz}\}$ orthonormal basis of $R^3$:

$$\vec{\phi} = (\phi^x, \phi^y, \phi^z)$$

2.7.1 Defining a global roughness criterion $R(\vec{\phi})$

As usual, the set of nodes $\Omega$ is split into two subsets I and L such that:

$$\begin{cases} \vec{\phi}_i \text{ is unknown} & \forall i \in I \\ \vec{\phi}_i \text{ is known} & \forall l \in L \end{cases}$$

The nodes $l \in L$ whose location $\vec{\phi}_l \in R^3$ is known will be called control nodes and the aim is to determine the location of the remaining points $i \in I$ in such a way that the following local criterion $R(\vec{\phi}|k)$ based on a given set of weighting coefficients $\{v^\alpha(k)\}$ is as small as possible:

$$R(\vec{\phi}|k) = \sum_{\alpha \in N(k)} v^\alpha(k) \cdot \vec{\phi}_\alpha^2$$

This criterion constitutes the vectorial form of the local DSI criterion. The associated global vectorial DSI criterion $R(\vec{\phi})$ is defined as follows where $\{\mu(k)\}$ are given non-negative weighting coefficients:

$$R(\vec{\phi}) = \Sigma \mu(k) \cdot R(\vec{\phi}|k)$$

Defining $R(\phi^x)$, $R(\phi^y)$ and $R(\phi^z)$ as previously:

$$\begin{cases} R(\phi^x) = \sum_k \mu(k) \cdot R(\phi^x|k) & \text{with: } R(\phi^x|k) = |\sum_{\alpha \in N(k)} v^\alpha(k) \cdot \phi_\alpha^x|^2 \\ R(\phi^y) = \sum_k \mu(k) \cdot R(\phi^y|k) & \text{with: } R(\phi^y|k) = |\sum_{\alpha \in N(k)} v^\alpha(k) \cdot \phi_\alpha^y|^2 \\ R(\phi^z) = \sum_k \mu(k) \cdot R(\phi^z|k) & \text{with: } R(\phi^z|k) = |\sum_{\alpha \in N(k)} v^\alpha(k) \cdot \phi_\alpha^z|^2 \end{cases}$$

Pythagoras' theorem yields:

$$R(\vec{\phi}) = R(\phi^x) + R(\phi^y) + R(\phi^z)$$

2.7.2 Allowing for linear constraints in a least squares sense

Consider the following matrices sized so that N is the total number of nodes of the set $\Omega$:

$$v = x, y, z: \begin{cases} [D_{i_v}^v] \text{ is an } N \times N \text{ diagonal non-negative semidefinite matrix,} \\ [A_{i_v}^v] \text{ is an } N \times N \text{ square matrix,} \\ B_{i_v}^v \text{ is an } N \text{ column matrix.} \end{cases}$$

To have the components $\phi^x, \phi^y$ and $\phi^z$ satisfy the following constraints $$[A_{i_x}^x] \cdot \phi^x \simeq B_{i_x}^x$$
$$[A_{i_y}^y] \cdot \phi^y \simeq B_{i_y}^y$$
$$[A_{i_z}^z] \cdot \phi^z \simeq B_{i_z}^z$$

the following criterion is introduced:

$$\begin{vmatrix} \rho(\vec{\phi}) = \rho(\phi^x) + \rho(\phi^y) + \rho(\phi^z) \\ \text{with: } \begin{cases} \rho(\phi^x) = \sum_{i_x} [A_{i_x}^x] \cdot \phi^x - B_{i_x}^x {}^2 D_{i_x}^x \\ \rho(\phi^y) = \sum_{i_y} [A_{i_y}^y] \cdot \phi^y - B_{i_y}^y {}^2 D_{i_y}^y \\ \rho(\phi^z) = \sum_{i_z} [A_{i_z}^z] \cdot \phi^z - B_{i_z}^z {}^2 D_{i_z}^z \end{cases} \end{vmatrix}$$

2.7.3 Solution of the problem

Among all the surfaces S interpolating the data $\{\vec{\phi}(l) = \vec{\phi}_l; l \in L\}$, the aim is to select the one minimizing the following criterion:

$$R^*(\vec{\phi}) = R(\vec{\phi}) + \rho(\vec{\phi})$$

It is easy to verify that this equation can be rewritten as follows:

$$\begin{vmatrix} R^*(\vec{\phi}) = R^*(\phi^x) + R^*(\phi^y) + R^*(\phi^z) \\ \text{with: } \begin{cases} R^*(\phi^x) = R(\phi^x) + \rho(\phi^x) \\ R^*(\phi^y) = R(\phi^y) + \rho(\phi^y) \\ R^*(\phi^z) = R(\phi^z) + \rho(\phi^z) \end{cases} \end{vmatrix}$$

Allowing for independence of the components $\phi^x, \phi^y$ and $\phi^z$:

$$R^*(\vec{\phi}) \text{ minimum} \iff \begin{cases} R^*(\phi^x) \text{ minimum} \\ R^*(\phi^y) \text{ minimum} \\ R^*(\phi^z) \text{ minimum} \end{cases}$$

Minimizing the vectorial DSI criterion is thus equivalent to minimizing the corresponding three DSI criteria applied to the three components of the current vector $\vec{\phi}$.

2.7.4 Note

If the surface S is composed of several disjoint patches the theorem explained in section 2.3 ensures that there exists a unique solution to the problem if at least one triangle apex within each patch has a known position.

2.7.5 Interactive use

In Geometric Modeling, the goal is to define interactively the geometric shape of the graph G associated with the set of nodes $\Omega$. To this end, it is assumed that an initial shape is known and the user moves some nodes and changes interactively some constraints (control nodes and fuzzy data); these modifications are then propagated to the nodes i∈I through the vectorial form of the DSI method.

As explained previously, this problem is broken down into three sub-problems corresponding to the three coordinates (x,y,z) and the best way to solve these three problems is to use the iterative algorithm associated with the local form of the corresponding DSI equations.

Between steps of the modeling process, not only can the position of the control nodes be modified but also the subset L itself can be changed if necessary; for example, to apply DSI only to a subset $\Gamma$ of nodes, it is necessary to choose L in such a way that $\Gamma \supset \bar{\Gamma}$ where $\bar{\Gamma}$ stands for the complementary set of $\Gamma$ in $\Omega$.

Moreover, because the problem is broken down into sub-problems solved independently and corresponding to the three coordinates, different subsets $L_x$, $L_y$ and $L_z$ can be defined for each coordinate if necessary; for example, if the (x,y) coordinates must not be modified it is sufficient for $L_x$ and $L_y$ to be equal to the whole set $\Omega$.

2.7.6 Allowing for fuzzy geometrical data

Initially, the DSI method was designed to model complex surfaces encountered in the field of natural sciences, for example in geology and biology. In this case, there is generally much imprecise data to take into account such as:

$$\begin{cases} \cdot \text{ fuzzy control nodes,} \\ \cdot \text{ fuzzy vectorial constraints.} \end{cases}$$

Fuzzy control nodes

By definition, a "fuzzy control node" is any node $\lambda \in I$ whose position $\vec{\phi}_\lambda$ is known as being approximately equal to a given vector $\vec{\tilde{\phi}}_\lambda$ with a given degree of certainty $\omega_\lambda^2$.

Referring to section 2.5.1, such fuzzy data can be taken into account with the DSI method by introducing the following constraints in the $R^*(\phi^x)$, $R^*(\phi^y)$ and $R^*(\phi^z)$ criteria:

$$\begin{cases} \phi_\lambda^x \simeq \tilde{\phi}_\lambda^x \\ \phi_\lambda^y \simeq \tilde{\phi}_\lambda^y \\ \phi_\lambda^z \simeq \tilde{\phi}_\lambda^z \end{cases}$$

Fuzzy vectorial constraints

In many applications it is necessary to control the vector $(\vec{\phi}_\mu - \vec{\phi}_\lambda)$ joining two nodes $\vec{\phi}_\lambda$ and $\vec{\phi}_\mu$ of a surface. By definition, such a constraint is called a "fuzzy vectorial constraint" if it must be satisfied with a given degree of certainty $\omega_{\lambda\mu}^2$. Some examples of constraints of this type are shown in FIG. 2.

Figure 2A:
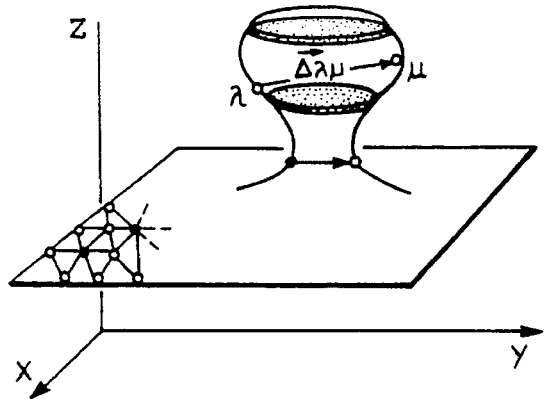
FIGS. 2(a) through 2(d) show four instances of controlling the shape of the surface using four different types of vector constraint; the vectors $\vec{\Delta}_{\lambda\mu}$ are assumed to be known directly in FIGS. 2(a) through 2(c) and known because they are orthogonal to a given vector $\vec{V}$ in FIG. 2(d)
Figure 2B:
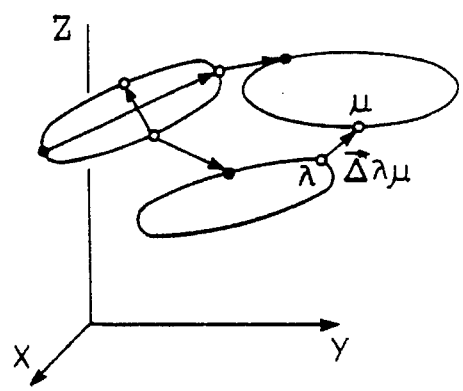

In practice, at least one of the two points $\vec{\phi}_\lambda$ and $\vec{\phi}_\mu$ has an unknown position, say the one corresponding to $\lambda \in I$, and two important cases have to be considered:

The first case corresponds to FIGS. 2a and 2b where the shape of an object must be controlled in such a way that $(\vec{\phi}_\mu - \vec{\phi}_\lambda)$ is equal to a given vector $\vec{\Delta}_{\lambda\mu}$.

Figure 2C:
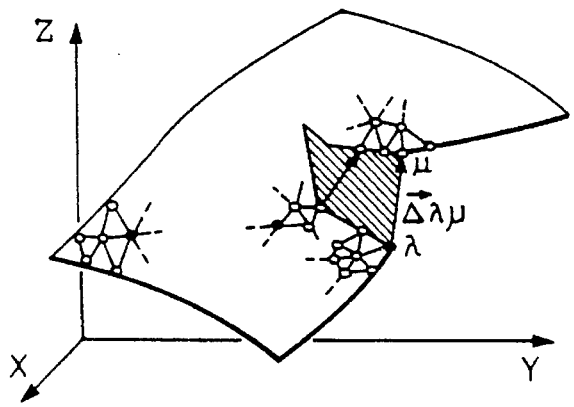
Figure 2D:
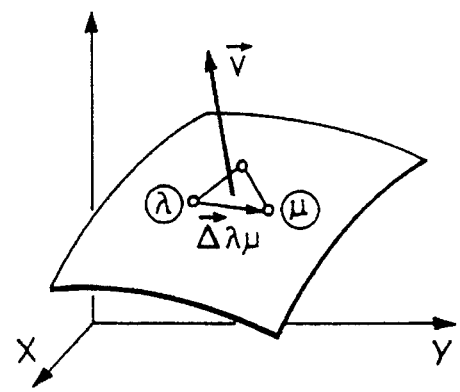

The second case corresponds to FIG. 2c where the shape of an object must be controlled in such a way that $(\vec{\phi}_\mu - \vec{\phi}_\lambda)$ is orthogonal to a given vector $\vec{V}$. This situation occurs when the vector normal to a surface is to be controlled; in this case, if $\vec{V}$ is the normal vector at node $\lambda$ of the surface, it is wise to control its orthogonality with all the vectors $(\vec{\phi}_\mu - \vec{\phi}_\lambda)$ for all $\mu \in N(\lambda)$.

Referring to section 2.5.2, the first case is easily taken into account in the DSI method by introducing the following constraints in the $R^*(\phi^x)$, $R^*(\phi^y)$ and $R^*(\phi^z)$ criteria with a weighting coefficient equal to $\omega_{\lambda\mu}^2$:

$$\begin{cases} (\phi_\mu^x - \phi_\lambda^x) \simeq \Delta_{\lambda\mu}^x \\ (\phi_\mu^y - \phi_\lambda^y) \simeq \Delta_{\lambda\mu}^y \\ (\phi_\mu^z - \phi_\lambda^z) \simeq \Delta_{\lambda\mu}^z \end{cases}$$

For the second case, the problem is not very different because:

$$(\vec{\phi}_\mu - \vec{\phi}_\lambda) \cdot \vec{V} \simeq 0 \iff \begin{cases} (\phi_\mu^x - \phi_\lambda^x) \simeq -\{V^y \cdot (\phi_\mu^y - \phi_\lambda^y) + V^z \cdot (\phi_\mu^z - \phi_\lambda^z)\}/V^x \\ (\phi_\mu^y - \phi_\lambda^y) \simeq -\{V^z \cdot (\phi_\mu^z - \phi_\lambda^z) + V^x \cdot (\phi_\mu^x - \phi_\lambda^x)\}/V^y \\ (\phi_\mu^z - \phi_\lambda^z) \simeq -\{V^x \cdot (\phi_\mu^x - \phi_\lambda^x) + V^y \cdot (\phi_\mu^y - \phi_\lambda^y)\}/V^z \end{cases}$$

In this case, the values $(\phi_\lambda^x, \phi_\lambda^y, \phi_\lambda^z)$ and $(\phi_\mu^x, \phi_\mu^y, \phi_\mu^z)$ on the righthand side of the equations can be set to the corresponding values inferred at the previous step of the iterative process; if $$\Delta_{\lambda\mu}{}^x = -\{V^y\cdot(\phi_\mu{}^y-\phi_\lambda{}^y)+V^z\cdot(\phi_\mu{}^z-\phi_\lambda{}^z)\}/V^x$$

$$\Delta_{\lambda\mu}{}^y = -\{V^z\cdot(\phi_\mu{}^z-\phi_\lambda{}^z)+V^x\cdot(\phi_\mu{}^x-\phi_\lambda{}^x)\}/V^y$$

$$\Delta_{\lambda\mu}{}^z = -\{V^x\cdot(\phi_\mu{}^x-\phi_\lambda{}^x)+V^y\cdot(\phi_\mu{}^y-\phi_\lambda{}^y)\}/V^z$$

the second case becomes identical to the first case.

Note

In allowing for fuzzy data as described above only one certainty factor $\omega_{\lambda\mu}{}^2$ is used for all three components of the constraints. In practice this is not mandatory and, because of the independence of the three components, it is always possible to use three different certainty factors $\omega_{\lambda\mu}{}^{x2}$, $\omega_{\lambda\mu}{}^{y2}$ and $\omega_{\lambda\mu}{}^{z2}$ corresponding to the three components.

2.8 Generalization

Before concluding, some straightforward generalizations of the approach are worth mentioning:

The DSI method can be used on any kind of polygonal facets. In practice, triangles are recommended since they are the simplest polygons and are easy to handle in a computer program.

The DSI method can be used to estimate polygonal curves in a 3D space; in this case, triangles are replaced by segments.

2.9 Conclusion

The local form of the DSI equation provides a simple and powerful tool for modeling complex surfaces encountered in Geology and Biology, for example. In particular:

There are no restrictions as to the mesh used to model a surface and it is possible to uses automatic algorithms to build them; for example, if the mesh is composed of triangles, it is possible to use algorithms derived from the Delaunay method (See [2] and [5]). Moreover, the size of the mesh can easily be fitted locally to the complexity of the surface.

The DSI method can cope with large quantities of precise or fuzzy data. This may be particularly useful in Natural Sciences where the aim is not to generate aesthetic surfaces but to fit precise and fuzzy data consistently.

The algorithm derived from local DSI equation is fast enough to allow interactive use.

Nothing has been said about the representation of the facets. Depending on the application, plane facets may suffice. However, facets can if necessary be represented by non-planar surface patches interpolating the nodes of the mesh (See [4]).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A process for modeling a surface representing an interface between two areas with different properties in a three-dimensional body, comprising the steps of:

measuring to obtain a set of geometrical data, from said interface of said three-dimensional body, relating to the surface and associated with respective points on said surface;

meshing the surface so that all said points are a subset of nodes of a mesh;

storing at a specific memory address for each node of the mesh, the following data:
first, second, and third coordinates,
a number of satellite nodes,
satellite node address data providing access to specific coordinates of said satellite nodes and consequently to satellite node related data relating thereto, and
geometrical data associated with said each node of the mesh;

for each node of the mesh, defining a local roughness index derived from a weighted sum of the coordinates of the node and of its satellites;

defining a global roughness index obtained by summing the local roughness indices associated with the nodes, and a global violation index of said geometrical data, to thereby generate a sum of said global roughness index and said global violation index;

fitting fitted coordinates of each node processed by an iterative method in which for each step of an iteration there is added a weighted combination of the coordinates of the node and of the satellites of said node and a combination of the geometrical data associated with said node, to thereby minimize said sum of the global roughness index and the global violation index; and creating a representation of the surface from the fitted coordinates of each node.

2. A process according to claim 1, wherein:

the surface is meshed using triangles.

3. A process according to claim 1 wherein:

the fitting step comprises three separate sub-steps respectively using the first, second, and third coordinates of the nodes and the coordinates of the satellite nodes corresponding thereto, respectively.

4. A process according to claim 1, wherein:

the geometrical data includes vector data between two given nodes.

5. A process according to claim 1, wherein:

the geometrical data includes data of a vector normal to the surface to be modeled.

6. A process according to any one of claims 4 to 5, wherein:

at least one geometrical datum is associated with a coefficient representing a certainty factor by which said at least one datum is known, the global violation index is a function of said certainty factors.

7. A process according to claim 1, further comprising the steps of measuring properties of the three-dimensional body in a region of at least one node of the mesh and storing the measured properties at addresses specific to the at least one node so as to obtain complementary data of the three-dimensional body.

8. A process according to claim 1, wherein:

for each local roughness index, a ratio between a first and a second weight of a corresponding node equals a negative of the number of satellite nodes.

9. A process according to claim 8, wherein:

said weighted combination uses substantially the same weighting as the ratio.

10. A process according to claim 1, wherein:

the summing of the local roughness indices is a weighted summing.

11. A process according to claim 10, wherein:

said weighted combination uses the weighting associated with the local roughness indices.

12. A process according to claim 1, wherein:
the three-dimensional body is a geological formation.

13. A process according to claim 1, wherein:
the surface represents variations of a property of a two-dimensional body in a vicinity of a plane intersecting said body, said property being represented by a remaining dimension, and a representation of the surface is used to optimize visualization of underground resources of said three-dimensional body, said three dimensional body being a geological formation.

14. A process according to claim 1, wherein:
the representation of the surface is a graphical representation on a flat medium.

15. A method according to claim 1, wherein:
the representation of the surface is a three-dimensional model.

16. A device for modeling a surface representing an interface between two areas with different properties in a three-dimensional body, comprising:

means for measuring to obtain a set of geometrical data, from said interface of said three-dimensional body, relating to the surface and associated with respective points on said surface;

means for meshing the surface so that all said points are a subset of nodes of a mesh;

means for storing at a specific memory address for each node of the mesh, the following data:
first, second, and third coordinates,
a number of satellite nodes,
satellite node address data providing access to specific coordinates of said satellite nodes and consequently to satellite node related data relating thereto, and
geometrical data associated with said each node of the mesh;

calculation means for fitting fitted coordinates of each node processed by an iterative method in which for each step of an iteration there is added a weighted combination of the coordinates of the node and of the satellites of said node and a combination of the geometrical data associated with said node, to thereby minimize a sum of a global roughness index obtained by summing local roughness indices associated with the nodes, each local roughness index derived from a weighted sum of the coordinates of the node and the coordinates of its satellites, and of a global violation index of said geometrical data; and means for creating a representation of the surface from the fitted coordinates of each node.

* * * * *